(12) United States Patent
Yodfat et al.

(10) Patent No.: US 9,662,440 B2
(45) Date of Patent: May 30, 2017

(54) SYSTEMS, DEVICES AND METHODS FOR SUSTAINED DELIVERY OF A THERAPEUTIC FLUID

(75) Inventors: Ofer Yodfat, Maccabim-Reut (IL); Gavriel J. Iddan, Haifa (IL); Avraham Neta, Gilon (IL)

(73) Assignee: Roche Diabetes Care, Inc., Indianapolis, ID (US)

( * ) Notice: Subject to any disclaimer, the term of this patent is extended or adjusted under 35 U.S.C. 154(b) by 87 days.

(21) Appl. No.: 12/004,837

(22) Filed: Dec. 20, 2007

(65) Prior Publication Data

US 2008/0215035 A1 Sep. 4, 2008

Related U.S. Application Data

(60) Provisional application No. 60/876,679, filed on Dec. 22, 2006.

(51) Int. Cl.
*A61M 5/158* (2006.01)
*A61M 5/142* (2006.01)

(52) U.S. Cl.
CPC ........ *A61M 5/158* (2013.01); *A61M 5/14248* (2013.01); *A61M 5/14232* (2013.01); *A61M 2005/14268* (2013.01); *A61M 2005/1581* (2013.01); *A61M 2005/1585* (2013.01); *A61M 2209/045* (2013.01)

(58) Field of Classification Search
CPC .... A61M 5/14248; A61M 2005/14252; A61M 2005/14268; A61M 2005/1587; A61M 2209/01; A61M 2205/50; A61M 39/0208; A61M 39/0247; A61M 2025/0266; A61M 5/158; A61M 5/14232; A61M 2005/1581; A61M 2005/1585; A61M 2209/045

USPC ............... 604/513, 288.01, 151, 180, 272
See application file for complete search history.

(56) References Cited

U.S. PATENT DOCUMENTS

| | | | |
|---|---|---|---|
| 3,631,847 A | 1/1972 | Hobbs | 128/2 R |
| 3,771,694 A | 11/1973 | Kaminski | 222/70 |
| 4,498,843 A | 2/1985 | Schneider et al. | 417/22 |
| 4,544,369 A | 10/1985 | Skakoon et al. | 604/155 |
| 4,657,486 A | 4/1987 | Stempfle et al. | 417/12 |
| 5,957,895 A | 9/1999 | Sage et al. | 604/181 |
| 6,302,866 B1 | 10/2001 | Marggi | |
| 6,485,461 B1 | 11/2002 | Mason et al. | 604/132 |

(Continued)

FOREIGN PATENT DOCUMENTS

| | | |
|---|---|---|
| JP | 11347120 A | 12/1999 |
| WO | WO 98/58693 | 12/1998 |

(Continued)

OTHER PUBLICATIONS

"Reservoir." Merriam-Webster Online Dictionary. 2010. Merriam-Webster Online. <http://www.merriam-webster.com/dictionary/reservoir>.*

(Continued)

*Primary Examiner* — Emily Schmidt
*Assistant Examiner* — Lauren M Peng
(74) *Attorney, Agent, or Firm* — Dinsmore & Shohl LLP

(57) ABSTRACT

Embodiments of the present invention are directed to devices, systems and methods for delivering therapeutic fluid (e.g., insulin) into the body, including a skin adherable cradle, for retaining a therapeutic fluid dispenser for delivering a therapeutic fluid to a user.

22 Claims, 56 Drawing Sheets

(56) References Cited

U.S. PATENT DOCUMENTS

| | | | |
|---|---|---|---|
| 6,562,023 B1* | 5/2003 | Marrs et al. | 604/533 |
| 6,564,093 B1* | 5/2003 | Tannenbaum et al. | 604/20 |
| 6,589,229 B1* | 7/2003 | Connelly | A61M 5/14248 |
| | | | 604/65 |
| 6,699,218 B2 | 3/2004 | Flaherty et al. | 604/131 |
| 6,723,072 B2 | 4/2004 | Mahoney et al. | 604/131 |
| 6,740,059 B2 | 5/2004 | Flaherty | 604/67 |
| 6,997,914 B2* | 2/2006 | Smith et al. | 604/288.04 |
| 2001/0053889 A1 | 12/2001 | Marggi et al. | |
| 2003/0130625 A1* | 7/2003 | Jacobson et al. | 604/253 |
| 2003/0199855 A1* | 10/2003 | Rogers et al. | 604/891.1 |
| 2004/0143216 A1* | 7/2004 | Douglas et al. | 604/116 |
| 2005/0101932 A1 | 5/2005 | Cote et al. | |
| 2005/0107743 A1 | 5/2005 | Fangrow, Jr. | |
| 2005/0171512 A1* | 8/2005 | Flaherty | 604/890.1 |
| 2006/0247574 A1* | 11/2006 | Maule | A61M 5/158 |
| | | | 604/93.01 |
| 2006/0264835 A1 | 11/2006 | Nielsen et al. | 604/174 |
| 2007/0073235 A1* | 3/2007 | Estes et al. | 604/151 |
| 2007/0106218 A1 | 5/2007 | Yodfat et al. | 604/131 |
| 2009/0163874 A1* | 6/2009 | Krag | A61M 5/14248 |
| | | | 604/180 |

FOREIGN PATENT DOCUMENTS

| | | |
|---|---|---|
| WO | WO 2006/108809 A1 | 10/2006 |
| WO | WO-2007052277 A1 | 5/2007 |
| WO | WO 2008/020447 A1 | 2/2008 |
| WO | WO-2006108809 A1 | 10/2008 |

OTHER PUBLICATIONS

"Reservoir." Webster's New World College Dictionary and the American Heritage Dictionary of the English Language. 2010. YourDictionary.com <http://www.yourdictionary.com/reservoir>.*

"Source." Webster's New World College Dictionary. 2010. YourDictionary.com <http://www.yourdictionary.com/source>.*

International Search Report, PCT Application No. PCT/IL2007/001578.

* cited by examiner

SYSTEMS, DEVICES AND METHODS FOR SUSTAINED DELIVERY OF A THERAPEUTIC FLUID

RELATED APPLICATIONS

The subject application claims priority under 35 U.S.C. §119(e) to U.S. provisional patent application No. 60/876,679, filed Dec. 22, 2006, the entire disclosure of which is herein incorporated by reference.

FIELD OF THE INVENTION

Embodiments of the present invention relate generally to a device and a method for sustained medical infusion of fluids to a patient's body and for connecting and disconnecting the device to and from the patient's body. More particularly, some embodiments of the present invention relate to a new configuration of a portable infusion patch-like device that can be disconnected from and reconnected to the patient's body as necessary or according to the patient's discretion.

BACKGROUND OF INVENTION

Medical treatment of some illnesses requires continuous drug infusion into various body compartments, which is carried out as subcutaneous and intra-venous injections. For example, diabetes mellitus patients require the administration of varying amounts of insulin throughout the day to control their blood glucose levels. In recent years, ambulatory portable insulin infusion pumps have emerged as a superior alternative to multiple daily injections of insulin. These pumps, which deliver insulin at continuous basal rates as well as in bolus volumes, were developed to liberate patients from repeated self-administered syringe injections, and allow them to maintain a near-normal daily routine. Both basal and bolus volumes must be delivered in precise doses, according to individual prescription, since an overdose of insulin could be fatal. Therefore, insulin injection pumps must feature high reliability, to prevent the unintentional delivery of an excess of insulin.

Several ambulatory insulin infusion devices are currently available on the market. Mostly, these devices have two parts: a durable portion, containing a pumping mechanism, a controller and electronics, and a disposable portion containing a reservoir, a needle/penetrating assembly (e.g., a cannula and penetrating/needle member), and a fluid delivery tube altogether referred to as the "infusion set". Usually, the patient fills the reservoir, attaches the infusion set to the exit port of the reservoir, and then inserts the reservoir into the pump housing. After purging air out of the reservoir, out of the tube and out of the needle, the patient inserts the needle assembly, penetrating member and cannula, at a selected location on the body, and withdraws the penetrating member while leaving the cannula within the body. To avoid irritation and infection, the subcutaneous cannula must be replaced and discarded after two to three days, together with the empty reservoir.

Examples of a first generation pump, which employs disposable syringe-type reservoir and tubes, were described in 1972, by Hobbs, in U.S. Pat. No. 3,631,847, and in 1973, by Kaminski, in U.S. Pat. No. 3,771,694, and later by Julius, in U.S. Pat. No. 4,657,486, and by Skakoon, in U.S. Pat. No. 4,544,369, each of which is incorporated by reference herein. The driving mechanism employed in these devices comprises a screw thread derived plunger controlling the programmed movement of a syringe piston. While these devices represent an improvement over multiple daily injections, unfortunately they are heavy, bulky, and must be carried in a pocket or attached to a belt. Consequently, the fluid delivery tube is long, usually more than 60 cm, to permit needle insertion in remote sites of the body. Furthermore, since the tubing is long and not discreet, this severely disturbs teenagers' body image and prevents the teenager patients from insertion in remote sites like buttocks and limbs. To avoid the tubing limitations, a second generation of insulin pump was devised, namely—skin adhered pumps. For the sake of brevity these pumps will be referred-to further as patch type pumps or simply patches.

These patches include a housing having a bottom surface adapted for contact with the patient's skin, a reservoir disposed within the housing, and an injection needle which is in fluid communication with the reservoir. These skin adhered devices should be disposed every 2-3 days like current pump infusion sets. This type of pump was described by Schneider, in U.S. Pat. No. 4,498,843, Burton in U.S. Pat. No. 5,957,895, Connelly, in U.S. Pat. No. 6,589,229, and by Flaherty in U.S. Pat. No. 6,740,059, each of which is incorporated by reference herein. Additional configurations of skin adhered pumps are disclosed in U.S. Pat. Nos. 6,723,072 and 6,485,461, which are incorporated by reference herein. In these configurations, the pump is adhered to the patient's skin for the entire time period of device usage and the needle emerges from the bottom surface of the device and is fixed to the device housing.

These second-generation skin adhered devices have several limitations:
- Disconnection and reconnection of the pump to the patient is impossible—while there exists several conditions such as hot showers, bath and sauna (cause insulin denaturation) as well as other activities during which disconnection of the pump is required. In some cases the patient wants to disconnect the pump for a short period and subsequently reconnect it just to free himself from the 24 hours a day/7 days a week life long connection.
- Waste of Insulin—In cases of site misplacement (scar tissue, bleeding, cannula kinking etc.) the entire device including reservoir, which is full of insulin should be disposed.
- These devices are expensive—the entire device including relatively expensive parts should be disposed every pump replacement. Thus the production cost is high and the final product price far exceeds Medicare allowable payments.
- These devices are bulky and heavy—The automatic insertion mechanism included within the device occupies substantial volume as described in U.S. Pat. No. 6,699,218, which is incorporated by reference herein. The patient must carry the heavy and bulky insertion mechanism during the entire usage of the pump.

In view of the foregoing, what is needed is an improved method and device for delivery of therapeutic fluid to the body.

SUMMARY OF THE INVENTION

Embodiments of the present invention provide a number of systems, apparatuses, devices and methods for delivering therapeutic fluid into the body of a user. The terms "system" and "apparatus" can be used interchangeably in some embodiments of the present invention. In some embodiments, a miniature portable programmable fluid dispensing patch type pump is provided that does not have long external tubing and can be attached to the patient at any desired location on the patient's body. Alternatively or additionally, the device allows for disconnection and reconnection to the patient to make possible temporary removal by the patient in cases such as hot bath, sauna, etc. Such disconnection and reconnection can be performed without harm various components of the patch, like the dispenser, the needle, nor the surrounding tissue and/or the patient. The device may be inserted into position manually, automatically, or based on a combination of manual and automatic means.

It is worth noting that the term "patch" according to embodiments of the present invention, may be understood to be a small sized infusion system/device, which is directly adherable to a user's (human body) skin. For example, in some embodiments, the "patch" is a credit card sized infusion device, with a thickness of between about 5 mm to about 25 mm in thickness, and preferably less than about 15 mm in thickness.

In some embodiments, the fluid delivery device of the invention comprises 3 units: a dispensing patch unit, a skin adherable unit and a remote control unit. The patch unit is connectable to and disconnectable from a skin adherable needle unit, and a remote control unit is capable of programming and data acquisition. Remote control unit, according to some embodiments of the present invention, includes any electronic unit that can include functionality for communication with the patch/infusion device, and may include watches, mobile telephones, personal computers, and the like.

Below is a description of each unit according to some embodiments of the invention:

1. Patch unit: comprising a driving and pumping mechanism (either separately provided or integral with one another), a reservoir and an exit port. The exit port allows connection of the patch unit to and disconnection from the needle unit. The exit port is provided with a small connecting lumen that can pierce a self sealable rubber septum. The connecting lumen allows fluid communication between the patch unit and the needle unit. The patch unit can be comprised of one part. In this configuration it contains the reservoir, tubes, batteries, driving and pumping mechanism(s), electronics and other auxiliary components e.g. an occlusion sensor. Alternatively, the patch unit can be comprised of two or more parts. In this configuration it may contain:
   a. Reusable part—contains the driving and pumping mechanism(s), electronics and other relatively expensive components e.g. an occlusion sensor.
   b. Disposable part—contains components such as the reservoir, tubes and batteries that can last until reservoir emptying, usually a few days.
2. Needle unit comprises the following:
   a. Cannula and penetrating member. The penetrating member is removed after insertion.
   b. Cradle: a flat sheet with an adhesive layer (and/or one portion of a hook and loop fastening system—e.g., Velcro®) facing the skin and with a connecting means on its upper side allowing connection and disconnection of the patch unit. Upon insertion of the cannula the cradle remains connected to the skin by virtue of adhesive layer. The cradle anchors the cannula and allows connection to the patch. The cradle can be integral with the cannula and well or it can be separate, a stand alone piece.
   c. Well: a tubular protrusion emerging upwardly from the cradle to allow alignment with the patch unit and appropriate connection between the needle and the patch unit as required for proper fluid delivery to the body.
3. Remote control unit comprising means (e.g., electronics, including a CPU) and one-way or two-way communication elements for wirelessly communicating with the patch unit) required for issuing instructions for programming fluid flow and for data acquisition.

It is worth noting, that the cradle, according to some embodiments, may be any structure which is adherable to a user of a medical device, and which can receive a medical device, and retain it so that it may be used by the user in its intended manner. Accordingly, in some embodiments, such a cradle (as described with reference to some of the embodiments of the invention described herein) allows repeated connection and disconnection of the medical device to/from the cradle, even while the cradle remains adhered to the user. Moreover, according to some embodiments, the cradle may be simply a substantially flat structure having a portion/side which includes adhesive to adhere the cradle to the user's skin (and, thus, retain/hold the medical device in position), and having a portion/side which is faces/lies-adjacent to the medical device. According to other embodiments, the cradle may also be a housing (e.g., "box" like structure having at least one opening to receive the medical device). For example, the housing may be a box, having a side which is substantially flat (or configured to the natural contour of a surface of the body), and which also includes a side which is capable of being open to (for example) slidably receive the medical device.

Some embodiments of the invention are directed to a therapeutic fluid infusion device cradle adherable to the skin of a user for retaining a therapeutic fluid dispenser for delivering a therapeutic fluid to a user. In such embodiments, the cradle includes a structure having a first surface configured for adhering to the skin of a user and having at least a portion of a second surface which substantially corresponds to at least a portion of a therapeutic fluid infusion device, at least one connecting area for connection with a corresponding connecting area of the infusion device, wherein connection between the two connecting areas enables the cradle and infusion device to be removably affixed to one another, an opening for receiving a fluid dispensing outlet of the infusion device and for receiving a cannula through which therapeutic fluid is delivered to the user, and an adhesive provided on at least a portion of the first surface of the cradle for adhering the cradle to the user.

Some embodiments of the invention are directed to a therapeutic fluid infusion system for delivering a therapeutic fluid to a human body. The system includes a first assembly having a cradle configured for adhesion to a cutaneous region of the human body, a cannula, and a self-sealing septum, wherein a distal portion of the cannula is configured for subcutaneous placement within the human body and wherein the self-sealing septum separates a proximal portion of the cannula from an external environment. The system also includes a second assembly configured for removable attachment to the first assembly, where the second assembly includes a pump, a reservoir for containing a therapeutic fluid, and a connecting lumen configured to penetrate the self-sealing septum in order to place the second assembly in fluid communication with the first assembly.

Some embodiments of the invention are directed to a method for delivering a therapeutic fluid to a human body, where the method includes securing a first assembly to a cutaneous region of the human body, penetrating the cutaneous region in order to place the first assembly in fluid communication with the human body, removably attaching a second assembly comprising the therapeutic fluid to the first assembly in order to place the second assembly in fluid communication with the first assembly, detaching the second assembly from the first assembly and substantially simultaneously with the detaching, sealing the first assembly to prevent fluid communication between the human body and an outside environment.

Some embodiments of the invention are directed to an apparatus for delivering a therapeutic fluid to a human body, the apparatus including means for securing a first assembly to a cutaneous region of the human body, means for penetrating the cutaneous region in order to place the first assembly in fluid communication with the human body, means for removably attaching a second assembly comprising the therapeutic fluid infusion device to the first assembly in order to place the second assembly in fluid communication with the first assembly, means for detaching the second assembly from the first assembly; and means for sealing the first assembly, substantially simultaneously with the detaching, to prevent fluid communication between the human body and an outside environment.

Some embodiments of the invention are directed to an inserter device for at least partially automating the placement of a needle assembly on a cutaneous region of the human body, the inserter device including a housing comprising an activation button/trigger/activation means, and a spring-loaded plunger (e.g., "driving/projection means" coupled to the activation trigger via an actuator (actuator means, e.g., elements/structural-members for connecting the trigger to the plunger). The plunger is configured for attachment to a needle assembly prior to a user pressing the activation button/trigger and for detachment from at least a portion of the needle assembly subsequent to the placement.

In some embodiments of the present invention, the patch unit can be also provided with appropriate means, e.g. buttons/switches, enabling issuing of flow instructions.

In some embodiments, a device is provided for sustained medical infusion with controlled rate injection of a fluid into a body.

In some embodiments, a device is provided for medical infusion that contains a dispensing patch that is thin, has no external tubing and can be connected to any part of the body. The device may include, for example, a reservoir, a delivery tube and an exit port enabling direct fluid communication with a skin adherable needle unit.

In some embodiments, the skin adherable unit comprises a subcutaneous cannula and a well that allows fluid communication between the patch unit and the subcutaneous compartment in the patient's body.

In some embodiments, a reusable part of a delivery device contains electronics, a driving and pumping mechanism and/or other relatively expensive components (e.g. a sensor for detection of occlusion in the delivery tube, and the disposable part contains reservoir, delivery tube and an exit port). Batteries can reside in the disposable part and/or in the reusable part.

In some embodiments, a device is provided that includes a dispensing patch unit that can be disconnected and reconnected.

In some embodiments, an infusion device is provided that includes 3 units—a remote control unit, a patch unit and a needle unit. The patch unit can be connected/disconnected to the needle unit and the needle unit is adherable to the skin. Infusion programming can be carried out by a remote control unit or by control buttons/switches on the patch.

In some embodiments, an infusion device is provided that includes a patch unit that can be connected to and disconnected from a needle unit. The needle unit comprises a skin compliant cradle that is associated with a cannula and a well.

In some embodiments, an infusion device is provided that includes a patch unit that can be connected to and disconnected from a skin compliant cradle. A needle unit that contains cannula and well can be inserted through the cradle into the skin.

In some embodiments, an infusion device is provided that includes a patch unit that is composed of at least one part. Another unit (needle unit) is composed of a cradle, a well, and a cannula. The cradle has an adhesive layer on its bottom side allowing retaining on the skin, and attachment means on its upper side allowing connection of the patch unit to the cradle. The well is connected at its lower side to the cannula and has a rubber septum (e.g., silicon rubber, chlorobutyl rubber, etc) at its upper side. The exit port of the patch unit is provided with a short needle for fluid communication between the patch unit and the well. This needle, which will be referred-to also as a "connecting lumen" allows multiple piercings of the rubber septum.

In some embodiments, a method is provided that allows infusion of a fluid into the patient's body through a flexible soft transdermal cannula. The cannula can be inserted in the patients body either manually or by a dedicated spring loaded inserter.

In some embodiments, a method is provided that allows adhering of a cradle to a patient skin by an adhesive, thus providing fixation of the cannula and a base for anchoring the patch unit.

In some embodiments, a method is provided that includes connecting the patch unit to and disconnecting the patch unit from the needle unit, connecting the exit port of the patch unit to the well, connecting the patch housing to the cradle and piercing the rubber septum by the connecting lumen.

Generally, some embodiments of the present invention provide a safe, simple, reliable and user-friendly device and method for connecting and disconnecting a patch unit to the patient while maintaining sterility and avoiding mechanical damage to the patient.

BRIEF DESCRIPTION OF DRAWINGS

Various objects and advantages of the present invention will be apparent from the following, non-limiting description of illustrative embodiments of the present invention.

DETAILED DESCRIPTION OF DRAWINGS

Figure 1A:
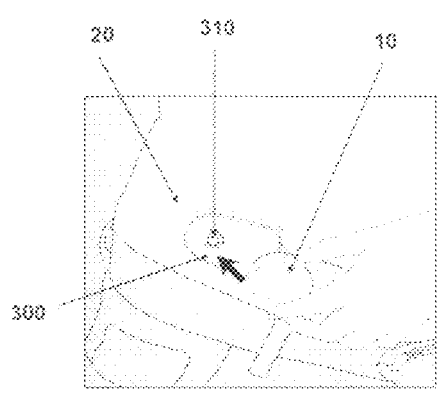
FIG. 1a-c are perspective views illustrating the use of a patch type fluid delivery device embodying the novel features of embodiments of the invention.

As shown in the drawings for purposes of illustration, embodiments of the present invention relate to a portable fluid infusion device. In some embodiments, the device can include 3 units: a remote control unit, a dispensing patch unit and a needle unit that is adherable to the skin at any desired location. In other embodiments, the device is composed of two units: a needle unit and a patch unit, without a remote control unit.

The patch unit may comprise a reservoir, a driving mechanism such as an electrical DC or stepper motor, a shape memory alloy actuator, or the like and/or a pumping mechanism such as a peristaltic pump, a syringe, or the like. The patch unit may also comprise a power supply means and electronic components.

The patch unit can be composed of one part or two parts, namely a reusable part and a disposable part and can be connected to and disconnected from the needle unit. In some embodiments, the needle unit comprises a penetrating member with connected thereto cannula, well and cradle.

One embodiment of a process for attaching the patch unit to the patient's body comprises the following main steps:

1. Needle unit insertion: The patient pricks the skin with the penetrating member to allow cannula placement in the subcutaneous compartment. The rigidly connected to the cannula cradle is adhered to the skin. After insertion, the penetrating member is withdrawn, the cannula remains in the body and the cradle remains adhered to the skin. Insertion of the needle unit can be done carried out manually or automatically with an inserter.

2. Patch unit attachment—the patient connects housing of the patch unit to the cradle such that the exit port of the patch unit is connected to the well of the needle unit.

Figure 1B:
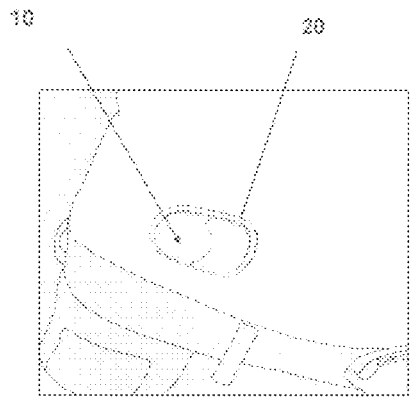
Figure 1C:
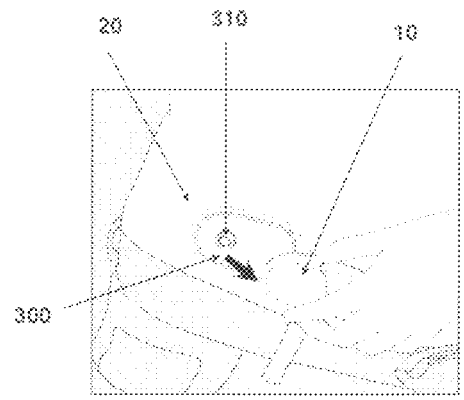

FIGS. 1A-1C show connection of the patch unit (10) to and disconnection of the patch unit (10) from the needle unit (20). FIG. 1A shows the needle unit (20) being attached to the body. In FIG. 1A are seen also, the cradle (300) and the well (310). After attaching the needle unit (20) to the body, the user may connect the patch unit (10) to the needle unit (20) by connecting the patch unit housing to the cradle and the exit port (not shown) of the patch unit to the well (310). FIG. 1B shows the patch unit (10) and the needle unit (20) being connected and attached to the patient body. The patch unit (10) and needle unit (20) after connection together constitute a fluid delivery device. FIG. 1C shows disconnection of the patch unit (10) from the needle unit (20). The process of connection and disconnection can be repeated many times according to the patient's discretion or as otherwise necessary.

Figure 2A:
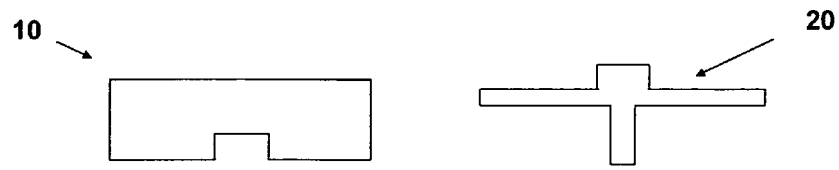
FIG. 2a-e are schematic descriptions of the connection and disconnection of patch unit to needle unit.
Figure 2B:
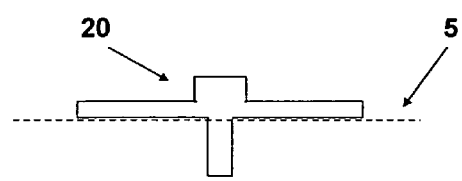
Figure 2C:
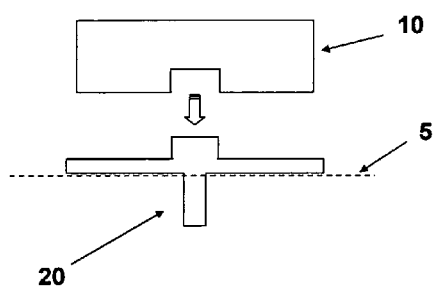
Figure 2D:
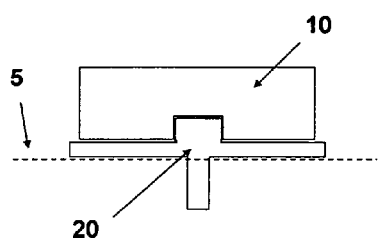
Figure 2E:
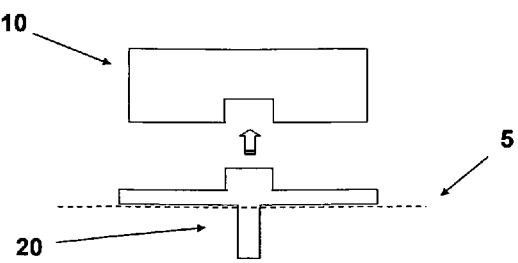

FIGS. 2A-2E show schematically two units of the fluid delivery device, the patch unit (10) and the needle unit (20). FIG. 2A shows the two units, the patch unit (10) and the needle unit (20). FIG. 2B shows the needle unit (20) adhered to the skin (5). FIG. 2C shows connection of the two units. FIG. 2D shows the two connected units brought into operation mode, and FIG. 2E shows disconnection of units. The two units can be repeatedly connected and disconnected.

Figure 3A:
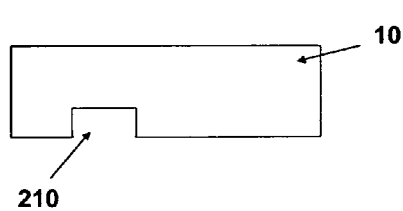
FIG. 3a-b are schematic descriptions of a single part patch unit (a) and a two-part patch unit (b).
Figure 3B:
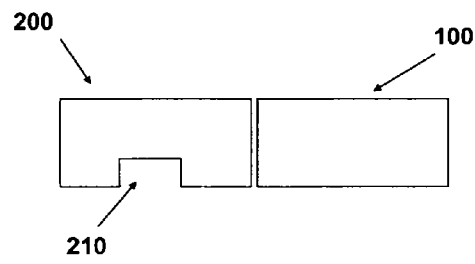

FIGS. 3A-3B show the patch unit (10) in more detail. The patch has on its lower surface an exit port (210). The patch unit (10) can be composed of a single part (FIG. 3A) or of two parts (FIG. 3B). The two part patch unit (10) is composed of a reusable part (100) and a disposable part (200) with an exit port (210). The exit port (210) allows fluid dripping during priming and fluid communication with the needle unit (20) during operation.

Figure 4A:
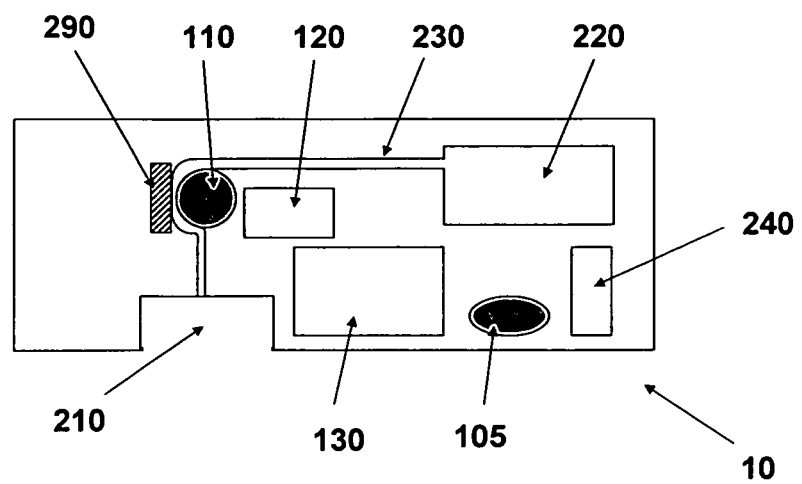
FIG. 4a-b are detailed schematic descriptions of a single part (a) and a two-part (b) patch unit employing a peristaltic pumping mechanism.
Figure 4B:
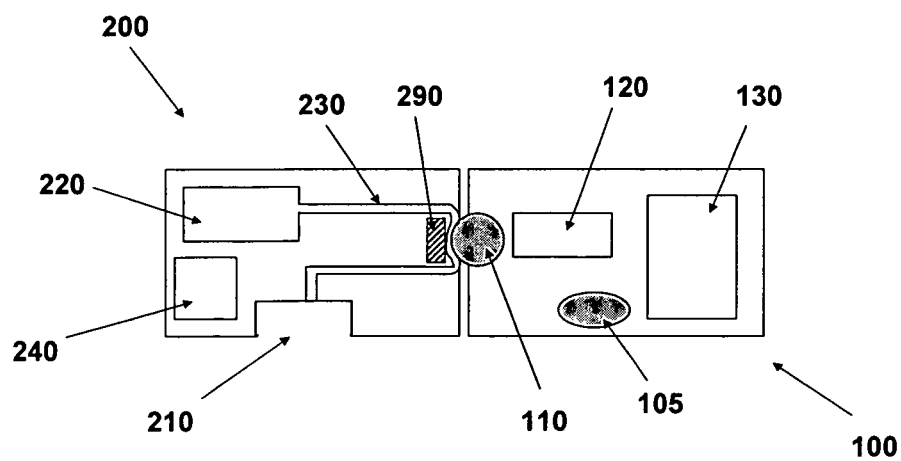

FIGS. 4A-4B show an embodiment of the patch unit (10) employing a peristaltic pump as a pumping mechanism for dispensing fluid to a patient body. FIG. 4A shows a single-part patch unit (10). The fluid is delivered from a reservoir (220) provided in the patch unit (10) through a delivery tube (230) to the exit port (210). The peristaltic pump comprises a rotary tooth wheel (110) provided with rollers and a stator (290).

Rotation of the wheel and pressing of rollers against the stator (290) periodically positively displaces fluid within the delivery tube (230) by virtue of a peristaltic motion. An example of suitable positive displacement pump is disclosed in commonly owned application U.S. Ser. No. 11/397,115, which is hereby incorporated by reference. Driving mechanism (120) is provided (e.g. a stepper motor, a DC motor, a SMA actuator or the like), which rotates the rotary wheel and is controlled by electronic components residing in the patch unit (10). Among such electronic components can be controller, processor and/or transceiver. The electronic components are schematically designated by a common numeral (130). An appropriate energy supply means (240) is also provided, which may include one or more batteries. Infusion programming can be carried out by a remote controller (not shown) having a bidirectional communication link with the transceiver provided in the patch unit (10). Alternatively or additionally, the infusion programming can be carried out by manual buttons/switches (105) provided on the patch unit (10).

FIG. 4B shows a two-part patch unit (10) comprised of a reusable part (100) and a disposable part (200). Reusable part (100) may comprise positive displacement pump provided with rotary wheel (110), driving mechanism (120) and/or electronic components (130). Disposable part (200) may include a reservoir (220), delivery tube (230), energy supply means (240), exit port (210) and/or stator (290). Fluid dispensing is possible after connecting the reusable part (100) with disposable part (200). This arrangement is described in above-incorporated U.S. Ser. No. 11/397,115.

Figure 5A:
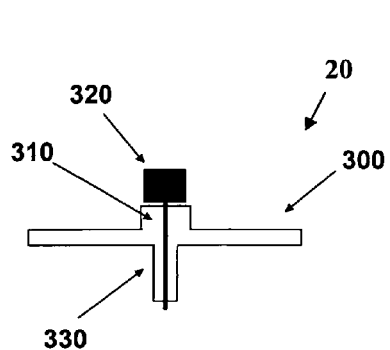
FIG. 5a-c are schematic descriptions of cradle adherence to skin and cannula subcutaneous placement.
Figure 5B:
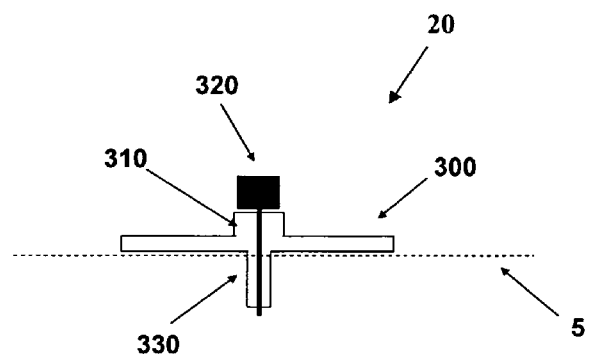
Figure 5C:
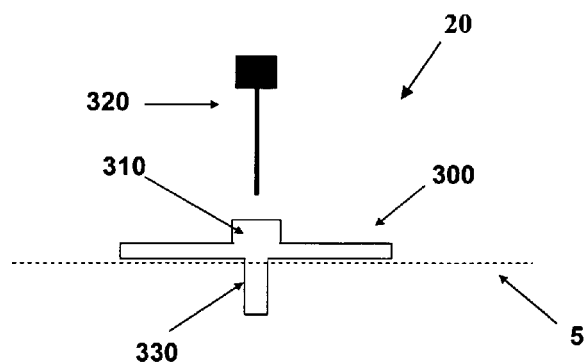

FIGS. 5A-5C show the needle unit (20). FIG. 5A shows the needle unit (20) before insertion. At this step the needle unit (20) comprises the following components: a cradle (300), a cannula (330), a penetrating member (320) and a well (310). FIG. 5B shows the needle unit (20) after it has been adhered to the skin (5). The cradle (300) is adhered to the skin (5) by virtue of adhesive layer, which is provided on the side of the cradle (300) that faces the skin (5). The cannula (330) and the penetrating member (320) are shown after they have been placed in the subcutaneous compartment of the patient's body. FIG. 5C shows a still further step, when the needle unit (20) remains adhered to the skin (5) and the cannula (330) remains within the subcutaneous compartment while the penetrating member (320) is being removed.

Figure 6A:
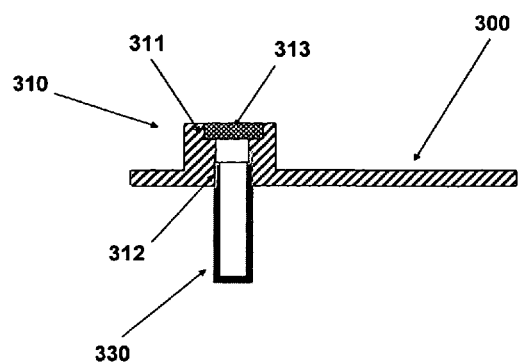
FIG. 6a-c are a transverse cross-sectional view (a), upper view (b) and perspective view (c) of needle unit including cradle, cannula and well (penetrating member not included).
Figure 6B:
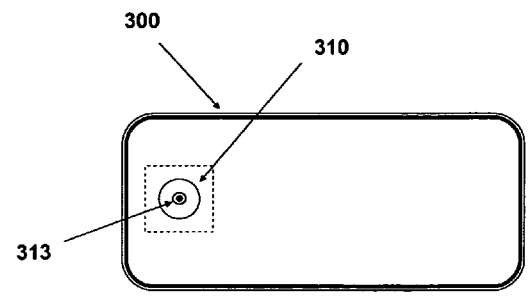
Figure 6C:
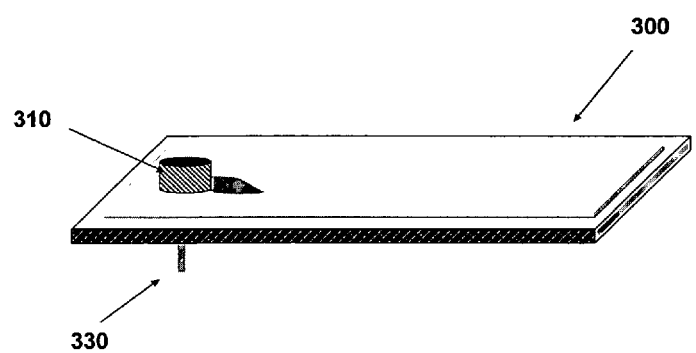

FIGS. 6A-6C show additional details of the needle unit (20): a cross sectional view (6A), an upper view (6B) and a perspective view (6C). The cradle (300) is configured as a flat and thin resilient sheet and it can be made for example from a polymer sheet having thickness of about 0.8 mm. The cradle (300) may be configured to any desired shape suitable for connection to the patch unit (10). To the bottom side of the cradle (300) that faces the skin (5) can be attached an adhesive tape (i.e. 3M™ Soft, conformable aperture nonwoven cloth tape) or this bottom side can be coated with a biocompatible epoxy layer enabling adherence to the skin (5). A protrusion (e.g., tubular protrusion) extends upwardly from the cradle (300) and forms the well (310). The well (310) may be positioned at the center, corner or any other location of the cradle (300). The upper end of the well (310) comprises a well inlet port (311), and the lower end of the well (310) comprises an outlet port (312) through which the cannula (330) is attached to the cradle (300). The inlet port (311) is sealed with a septum (313) that can be made of any self-sealable material (i.e. silicon rubber). The septum (313) can be pierced many times by a connecting lumen (250) provided in the patch unit (10) as will be described in greater detail below with reference to FIG. 17. The septum (313) keeps the well (310) sealed after withdrawal of the penetrating member (320) as shown in FIG. 7.

Figure 7A:
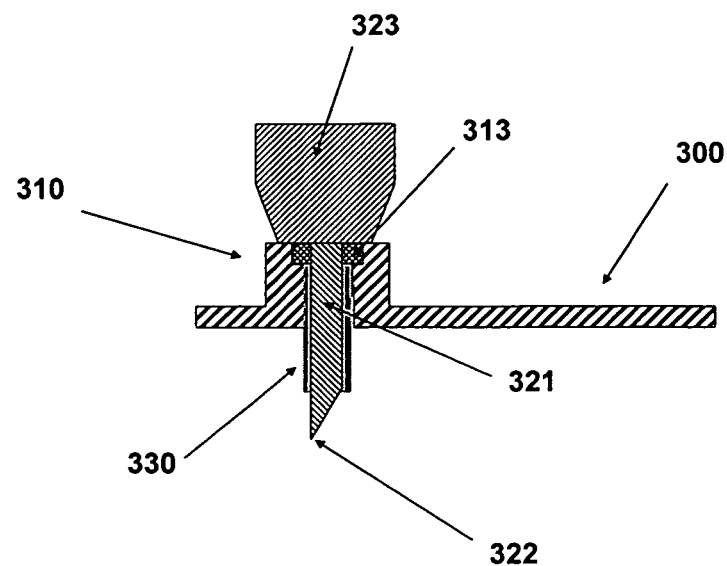
FIG. 7a-d are transverse cross-sectional views of a mounting procedure of a needle unit, including cradle adherence and cannula placement, Where the needle unit is a single integral part.
Figure 7B:
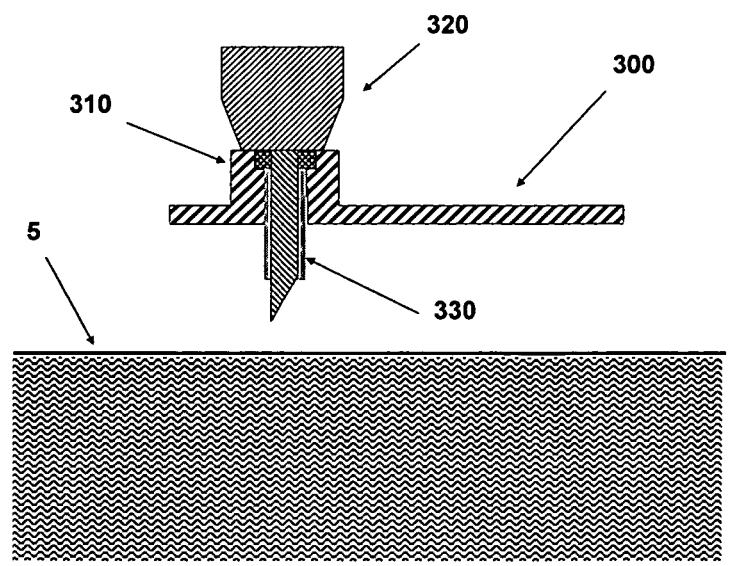
Figure 7C:
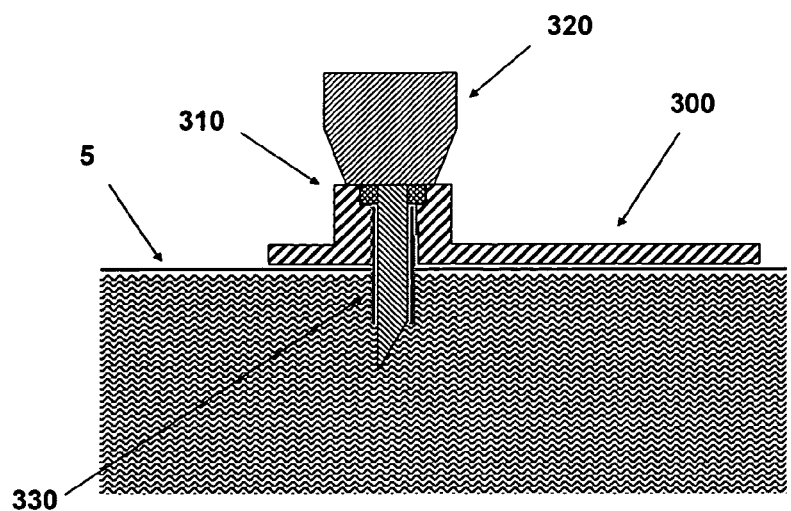
Figure 7D:
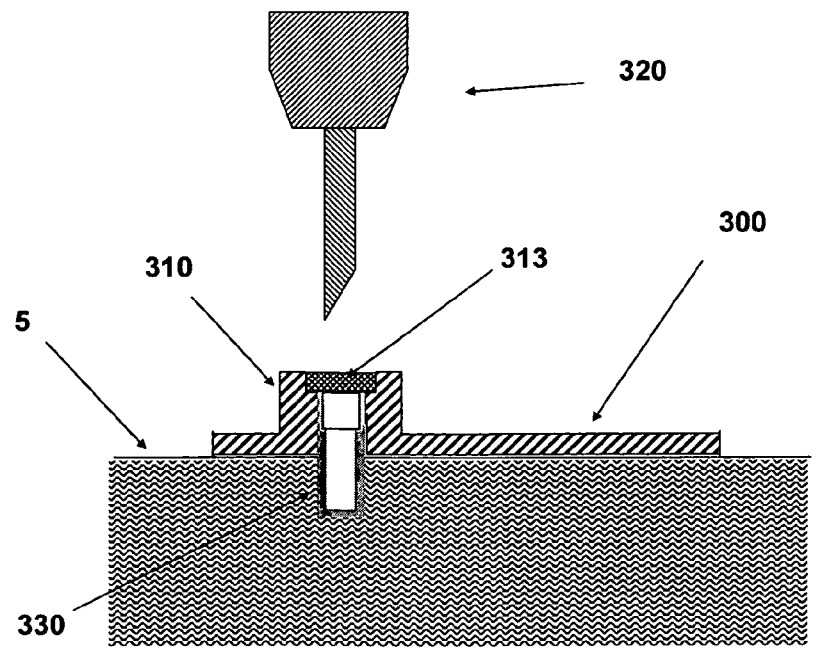

FIGS. 7A-7D shows how the needle unit (20) is attached to the body of a patient. The attachment procedure includes insertion of the cannula (330) and subsequent adherence of the cradle (300) to the skin (5). FIG. 7A shows the needle unit (20) before attachment. At this step the needle unit (20) includes cannula (330), cradle (300), well (310) and penetrating member (320). The penetrating member (320) includes a penetrating dagger (321) having a sharp tip (322) and a grip portion (323). The penetrating member (320) punctures the self-sealable septum (313) and displaces the cannula (330) towards the skin (5) while the sharp tip (322) pierces the skin (5) and the cannula (330) penetrates the subcutaneous compartment under the skin surface. FIG. 7B shows the needle unit (20) before insertion, i.e. just before the penetrating member punctures the skin and the cannula penetrates the subcutaneous compartment. FIG. 7C shows the needle unit (20) after insertion. The cradle (300) is adhered to the skin (5) and the cannula (330) and penetrating member (320) are subcutaneously inserted. FIG. 7D shows the needle unit (20) adhered to the skin (5) and the penetrating member (320) removed from the needle unit (20). The well remains to be sealed by the septum (313) after penetrating member (320) withdrawal.

In a further embodiment the needle unit can be attached to the skin automatically by means of an inserter.

Figure 8A:
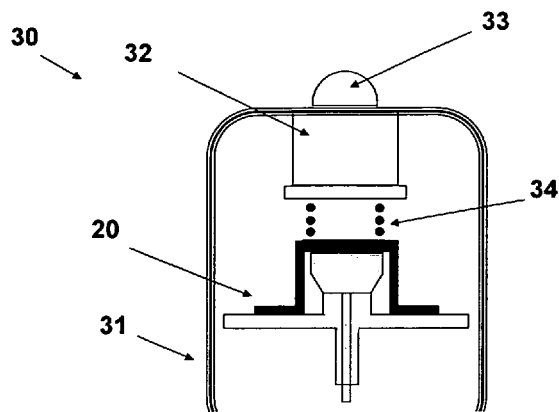
FIG. 8*a-f* are schematic cross-sectional views of an inserter used for cradle and cannula placement, where the needle unit is concealed within the inserter.
Figure 8B:
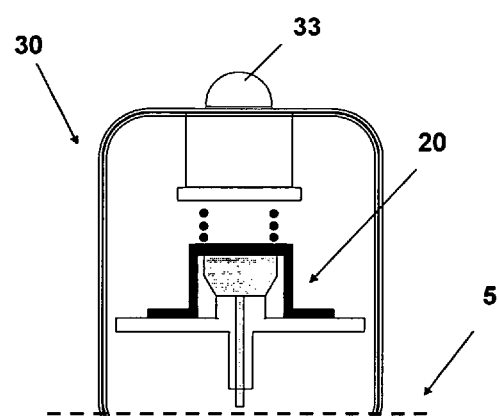
Figure 8C:
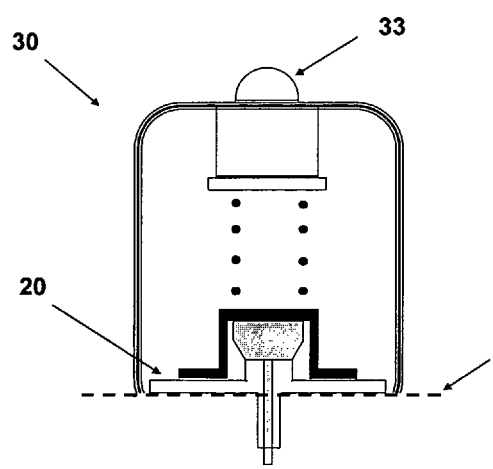
Figure 8D:
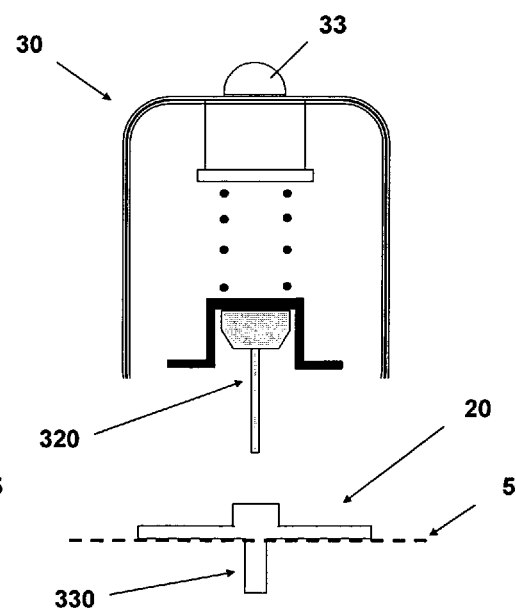
Figure 8E:
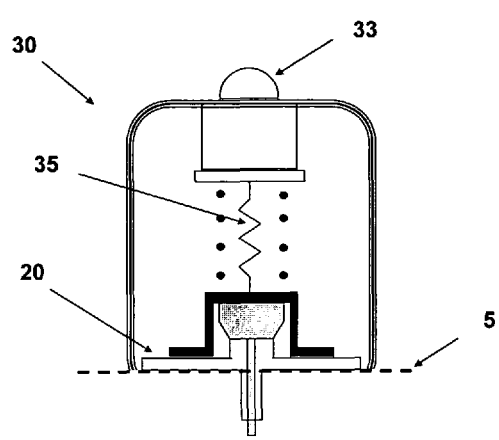
Figure 8F:
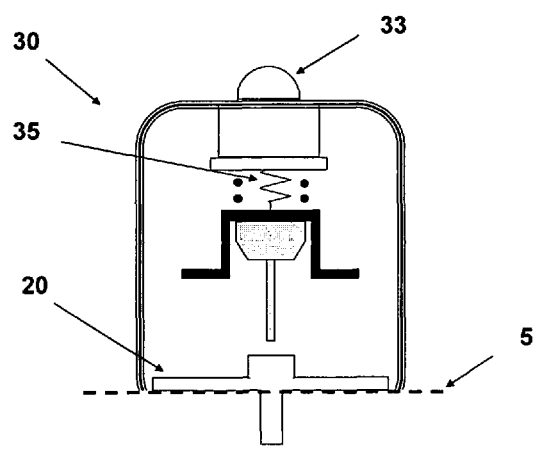

FIGS. 8A-F show an automatic insertion of the needle unit (20) by using an inserter (30). In some embodiments, the inserter (30) has a cup-shaped body. As shown in FIG. 8A, the inserter (30) comprises a cup-shaped body portion (31), an actuation mechanism (32) e.g. an actuator, an activation button/trigger (33) and a spring biased plunger element (34). The needle unit (20) is fully concealed within the inserter's body portion (31). FIG. 8B shows how the inserter (30) is located on the skin (5) before insertion. By triggering the activation button/trigger (32) the needle unit (20) is fired towards the skin (5). FIG. 8C shows the needle unit (20) being fired and attached to the skin upon triggering the activation button/trigger (33). FIG. 8D shows withdrawal of the inserter (30), while leaving the needle unit (20) in place. FIGS. 8E-F show an alternative embodiment, in which penetrating member (320) is being automatically withdrawn from the needle unit (20). In this embodiment the inserter is provided with a retraction spring (35), which retracts the penetrating member (320).

FIG. 8e shows the needle unit (20) placement following button/trigger (33) depression. The retraction spring (35) is extended. FIG. 8f shows penetrating member (320) withdrawal by the retracted spring (35), leaving the needle unit (20) in place.

Figure 9A:
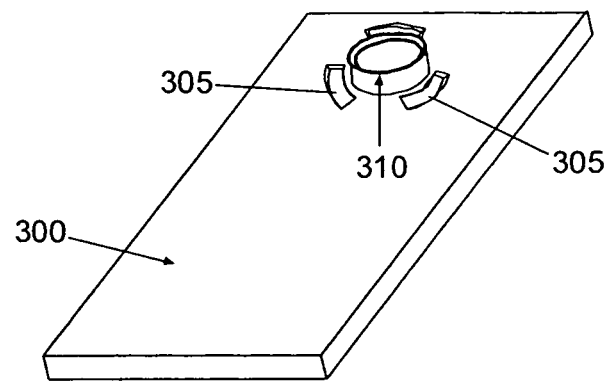
FIG. 9*a-b* are perspective (a) and upper (b) views of the cradle. In this configuration the cradle slides over inserter's legs.
Figure 9B:
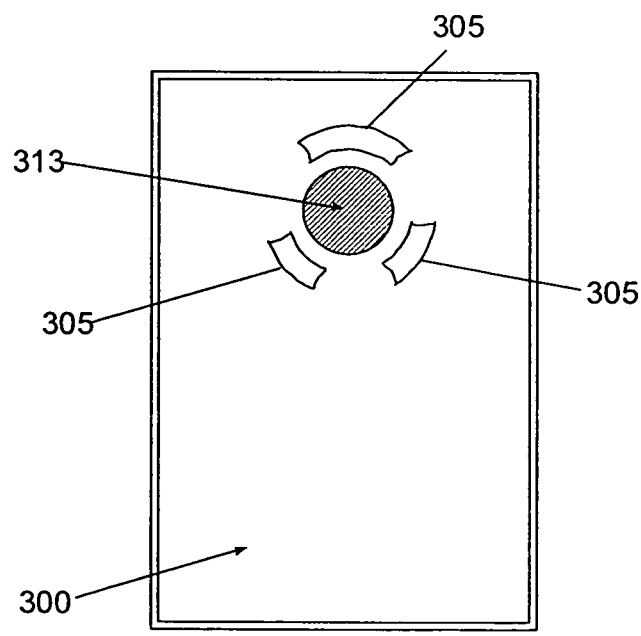

FIGS. 9A-9B show another embodiment of the inserter. FIGS. 9A-9B show the cradle (300) provided with the well portion (310) protruding therefrom and sealed by a septum (313). In this embodiment the cradle (300) is provided with arcuate discrete slits (305) formed on the cradle's upper face and surrounding the well portion (310).

Figure 10A:
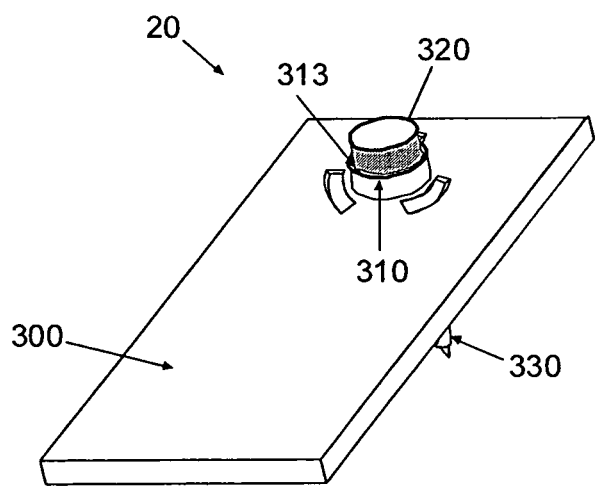
FIG. 10*a-g* are perspective views illustrating an inserter used for cradle and cannula placement—cradle slides over inserter's legs.
Figure 10B:
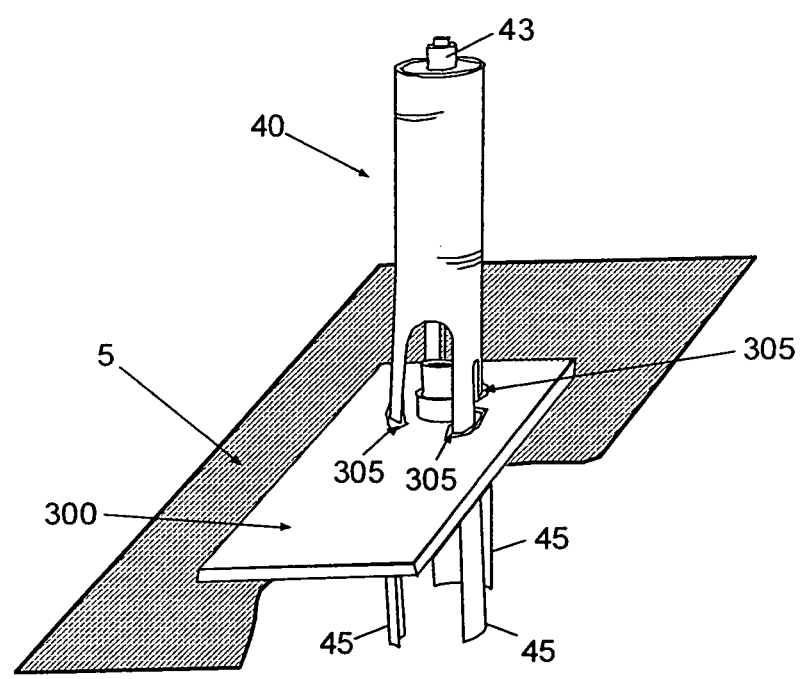
Figure 10C:
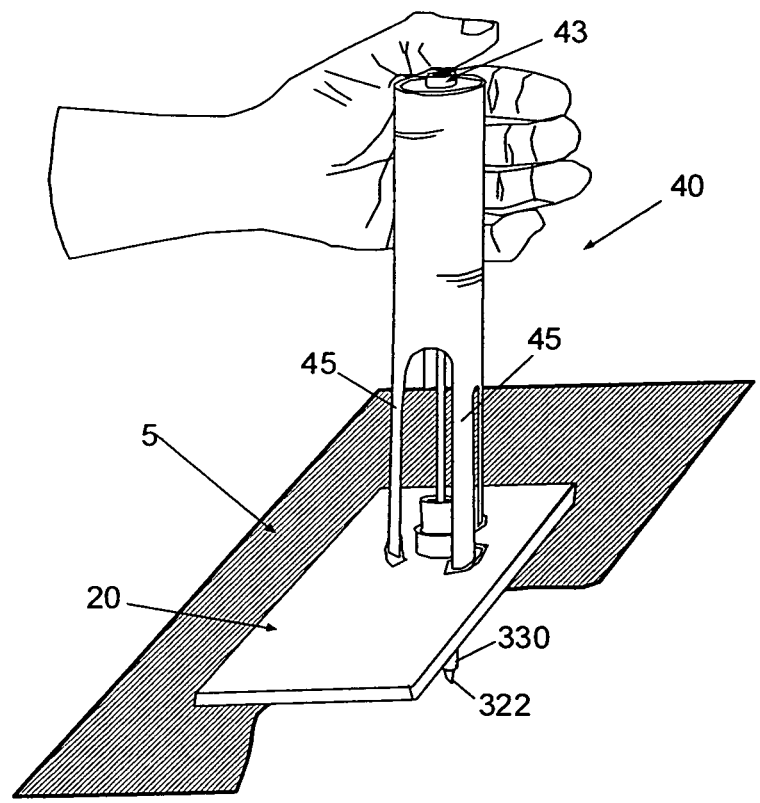
Figure 10D:
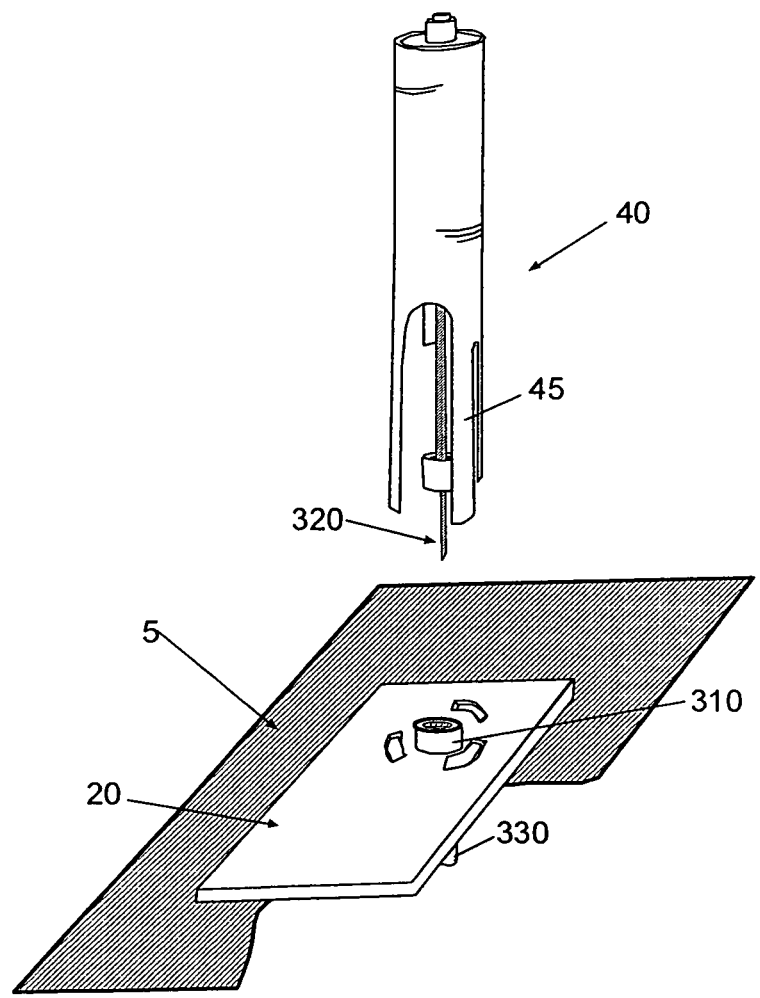
Figure 10E:
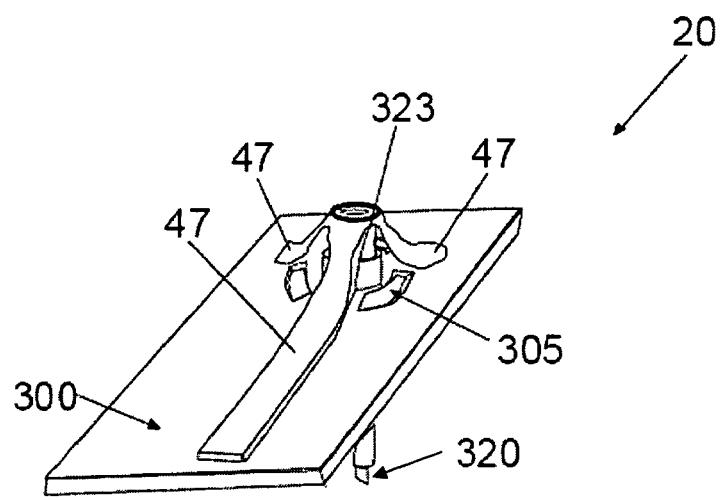

FIG. 10A shows the needle unit (20) comprising cradle (300) with the penetrating member (320) inserted within the well portion (310). Now, the needle unit (20) is ready for loading into inserter. In FIG. 10B is shown how the needle unit (20) is loaded into inserter (40). It is seen that the inserter is provided with legs (45) which are intended for entering into slits (305). FIG. 10B shows the inserter with needle unit (20) loaded therein ready for firing towards the skin (5). By triggering the activation button/trigger (43) the needle unit (20) can be fired towards the skin (5). FIG. 10C shows the needle unit (20) being fired and attached to the skin (5) upon triggering the activation button/trigger (43). FIG. 10D shows automatic withdrawal of the inserter (40) including penetrating member (320), while leaving the needle unit (20) in place. Since cradle (300) is configured as a flat and thin resilient sheet having thickness of about 0.8 mm, it may be difficult to prevent crumpling of the cradle (300) and ensure a uniform horizontal spreading of the cradle surface, which is crucial for a reliable adherence of the cradle (300). FIG. 10E shows an embodiment of the needle unit (20) provided with a few strips (47) which prevent crumpling (i.e., crumpling prevention means) of the cradle surface during firing of the needle unit (20). The strips (47) are connected by their one end to the grip portion (323) of the penetrating member (320).

Figure 10F:
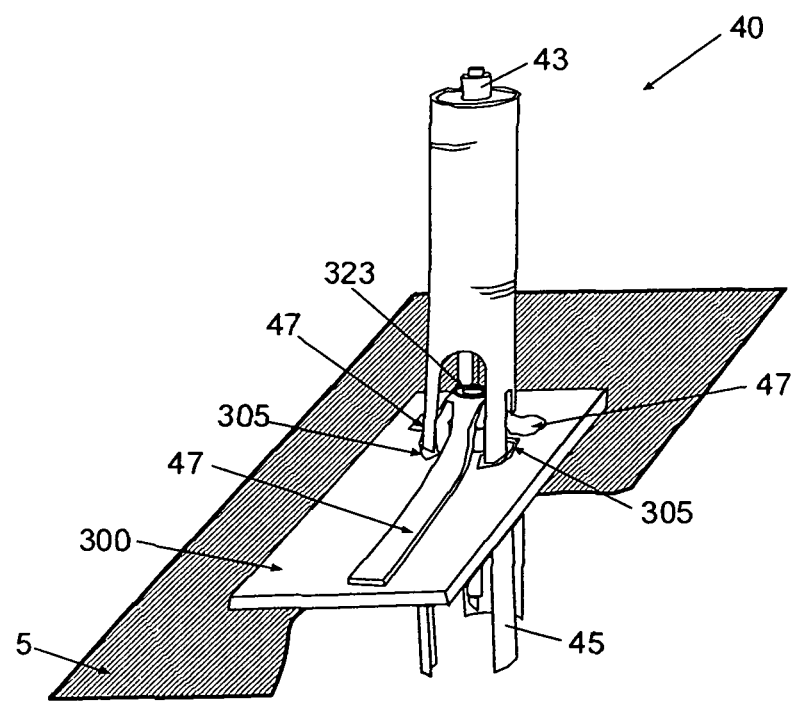
Figure 10G:
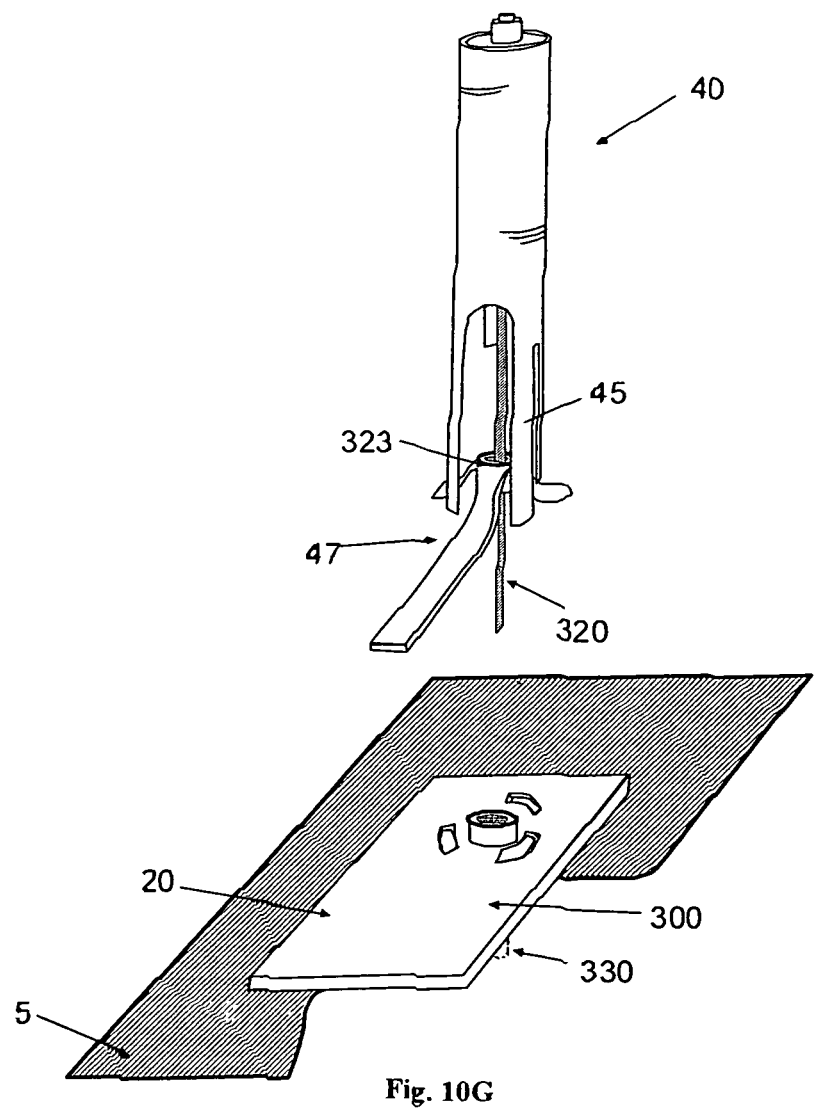

The strips (47) are slightly adhered to the cradle (300) by glue and are spread across the upper surface of the cradle (300). It is preferable if the strips (47) are located between adjacent arcuate slits (305). The width, thickness and rigidity of the strips (47) are selected to ensure that the cradle (300) remains in horizontal position during firing and does not crumple. FIG. 10F shows the needle unit (20) provided with strips (47) and being loaded within the inserter (40). It is seen that legs (45) pass through slits (305). Strips (47) ensure spreading of the cradle (300) without crumpling. FIG. 10G shows the next step in which the inserter (40) is withdrawn. The strips (47) disconnect from the cradle (300) and remain attached to the grip portion (323) when the inserter is evacuated from the cradle (300).

FIGS. 11A-11F show another embodiment of the needle unit. In this configuration the needle unit comprises two parts as follows:
1. The cradle part provided with Cradle base;
2. The penetrating cartridge part comprising:
   a. Well portion (sealed by a self-sealable septum)
   b. Cannula
   c. Penetrating member (the dagger and the grip)

Figure 11A:
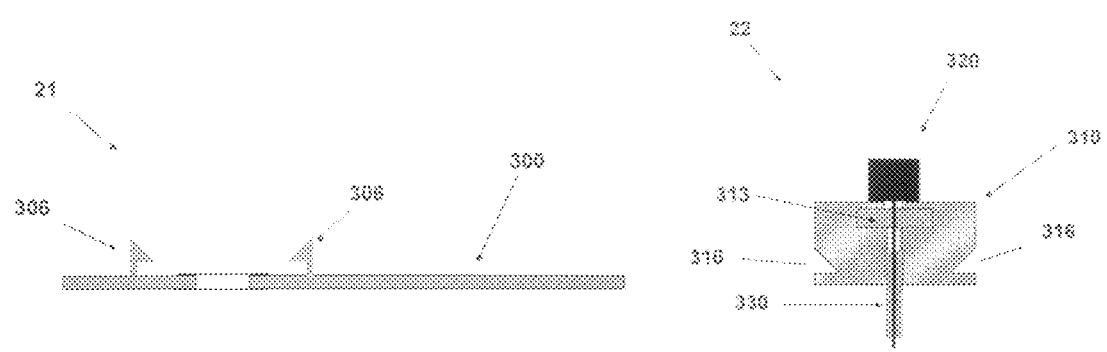
FIG. 11*a-f* are transverse cross-sectional views of a mounting procedure of a needle unit, including cradle adherence and cannula placement, where the needle unit comprises a cradle part and a penetrating cartridge part.

FIG. 11A shows the two parts of the needle unit (20) before insertion—the penetrating cartridge part (22) and the cradle part (21). The cradle part (21) comprises the cradle base (300) and connecting latches (306), which are situated around an opening made in the cradle base (300). The penetrating cartridge part (22) comprises well portion (310), lateral recesses (316) made in the well portion, septum (313), cannula (330) and penetrating member (320). The amount of recesses and their location should allow snapping of the latches on the recesses when the penetrating cartridge part (22) approaches the cradle part (21). By virtue of this provision a reliable securing of the penetrating cartridge part on the cradle part is provided.

Figure 11B:
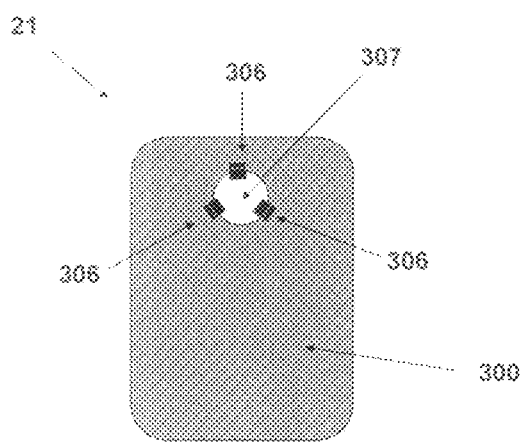
Figure 11C:
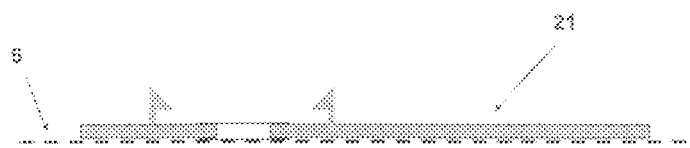
Figure 11D:
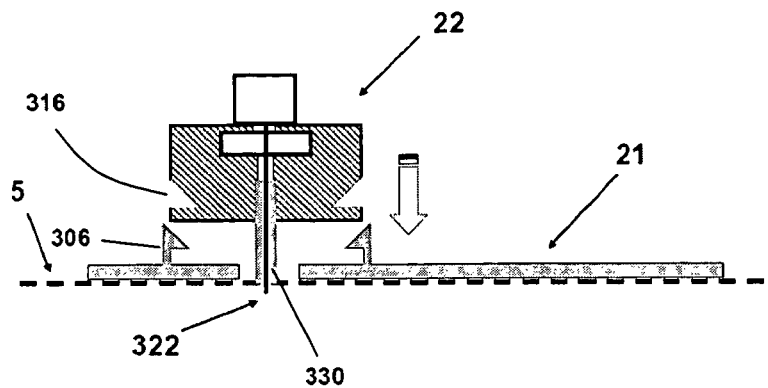

FIG. 11B shows an upper view of the cradle part (21) including cradle base (300) and three connecting latches (306), which are situated symmetrically around the opening (307). FIG. 11C shows the cradle part (21) attached to the patient skin (5). The attachment can be achieved by gluing with adhesives or by other means known in the art. It will be appreciated that an adhesive layer should be put on that side of the cradle base, which faces the skin. FIG. 11D shows how the penetration cartridge part (21) is approaching the cradle part (21) and latches (306) are about to snappingly engage the recesses (316). Upon engagement the sharp tip (322) of the penetrating member pricks skin (5) and cannula (330) penetrates the body.

Figure 11E:
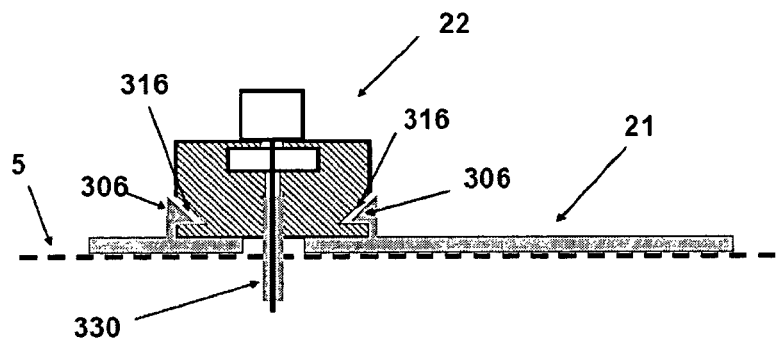
Figure 11F:
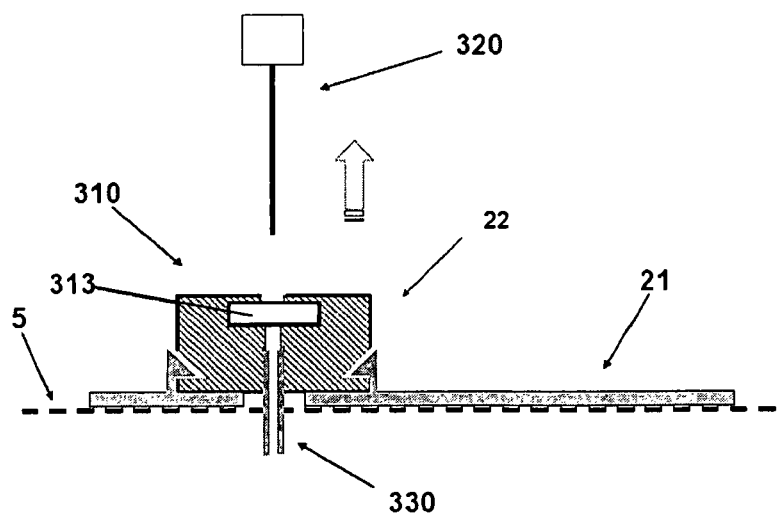

FIG. 11E shows the penetration cartridge part (22) connected to the cradle part (21). FIG. 11F shows the removal of the penetrating member (320) from the penetrating cartridge part (22). The cradle part (21) remains adhered to the skin (5) and the cannula (330) remains in the body. The self-sealable septum (313) of the well portion (310) allows for repeated connection/disconnection of the connecting lumen of the patch unit (10) and prevents leaking and penetration by contaminants, as shown in FIG. 17.

Figure 12A:
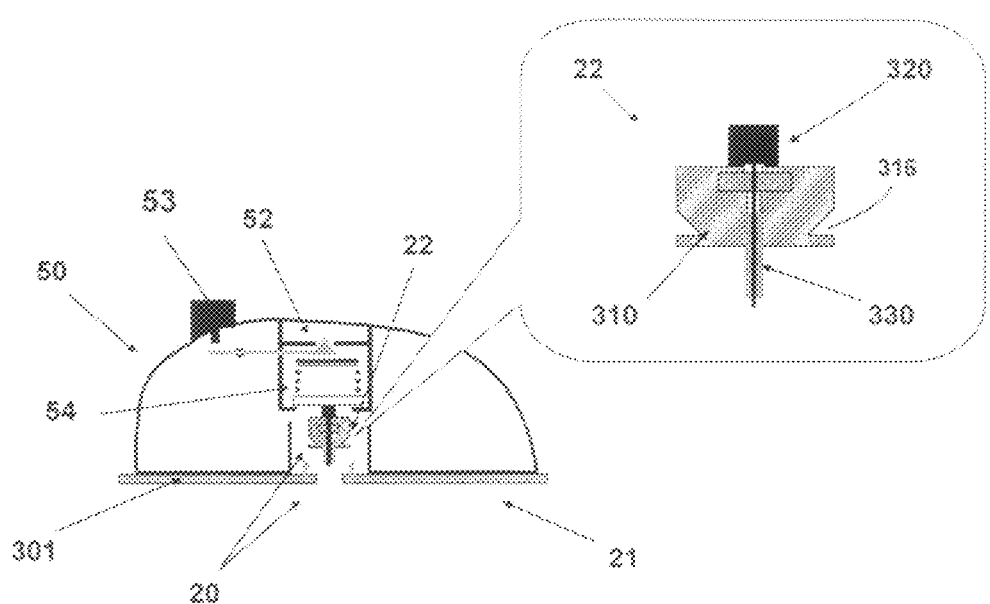
FIG. 12*a-d* are cross-sectional views of an embodiment of an inserter configured as a computer mouse. The inserter is used for cradle and cannula placement. The needle unit comprises a cradle part and a penetrating cartridge part.

FIGS. 12A-12D show an embodiment of an inserter (50) for use with the two part needle unit (20). The inserter facilitates adhesion of the cradle part (21) to the skin (5) and allows automatic connection of penetrating cartridge part (22) with the base cradle part (21). In this embodiment the cradle base part (21) is first attached to the skin and consecutively cartridge part (22) is fired by the inserter (50) toward the cradle base part (21) so as to connect the cradle base part (21) with the penetrating cartridge part (22). FIG. 12A shows inserter (50) and the two part needle unit (20) that comprises cradle part (21) and penetrating cartridge part (22). The figure shows the situation before insertion. The inserter (50) is provided with an actuation mechanism (52) employing plunger-spring element (54) and actuation button/trigger (53). The inserter is loaded with penetrating cartridge part (22). The penetrating cartridge part (22) comprises well portion (310), cannula (330) and penetrating member (320).

Figure 12B:
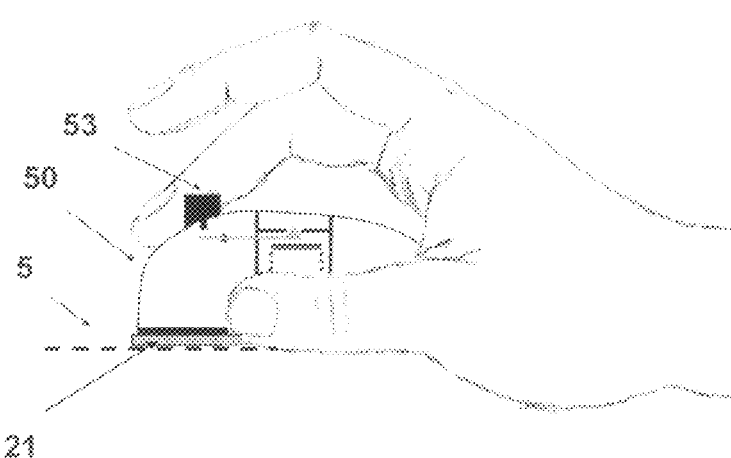
Figure 12C:
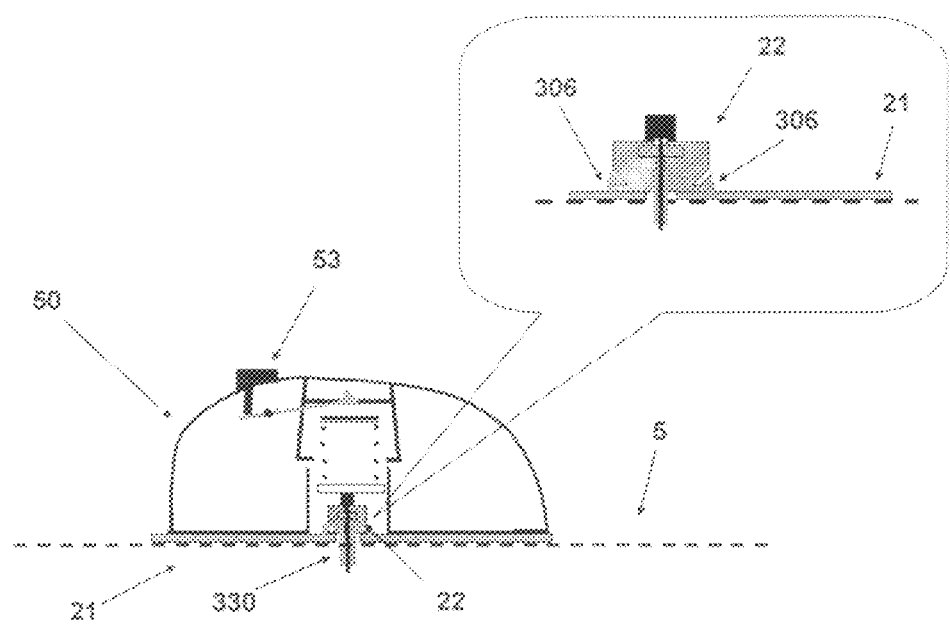
Figure 12D:
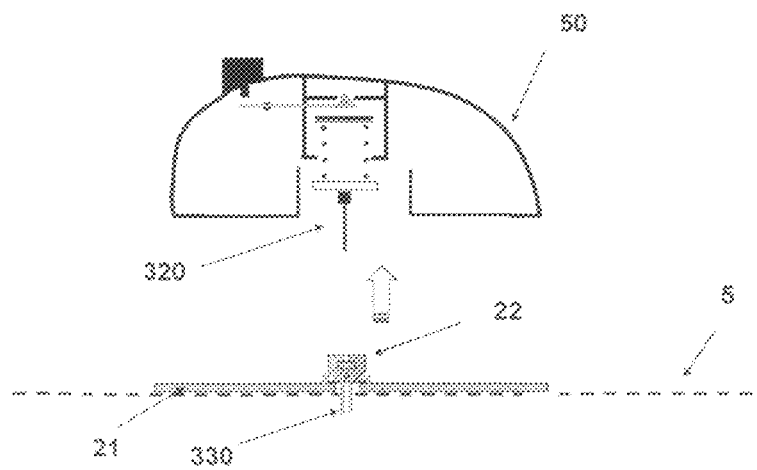

The cradle part (21) comprises cradle base (300) which upper side is relatively glued (or otherwise secured) to the inserter's bottom side. FIG. 12B shows the cradle part (21) attached to the patient skin (5). The attachment can be done by adhesives or by other means known in the art. Adherence is ensured by pressing the inserter (50) toward the skin. FIG. 12C shows the inserter (50) after the actuation button/trigger (53) is pressed and the penetrating cartridge part has been fired. Upon firing the penetrating cartridge part (22) is connected to the cradle part (21) by virtue of snapping engagement between latches (306) and depressions (316) made on the well portion (310) of the penetrating cartridge part (22). FIG. 12D shows still further step, when the inserter (50) along with the penetrating member (320) is being automatically removed from the skin (5). The cradle part (21) remains stay adhered to the skin (5) and the cannula (330) remains inserted within body.

FIGS. 13A-13G show another embodiment of a needle unit (20) which is intended for manual insertion mode. In this configuration the needle unit (20) also comprises two parts as follows:
1. The cradle part composed of:
   a. Cradle base
   b. Well portion; and
   c. Self-sealable septum
2. The penetrating cartridge part composed of:
   a. Cannula; and
   b. Penetrating member (the dagger and the grip).

Figure 13A:
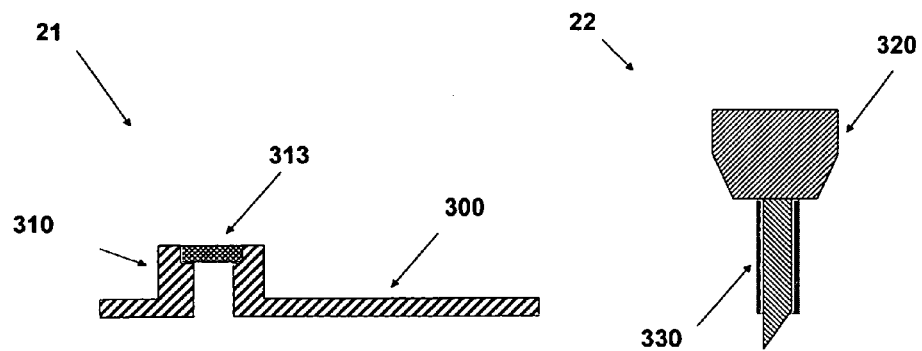
FIG. 13*a-g* are cross-sectional schematic views of a mounting procedure for a needle unit including cradle adherence and cannula placement, where the needle unit comprises a cradle part and a penetrating cartridge part.
Figure 13B:
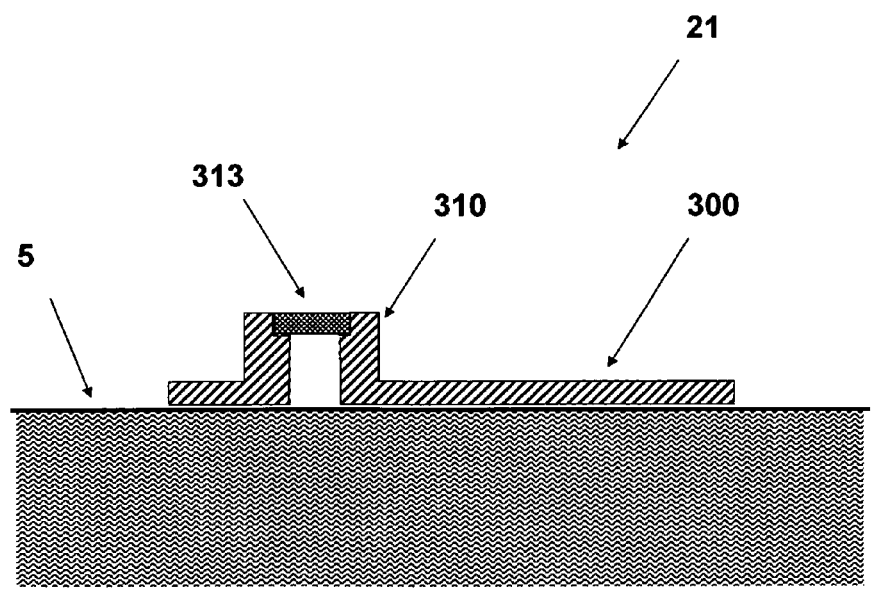
Figure 13C:
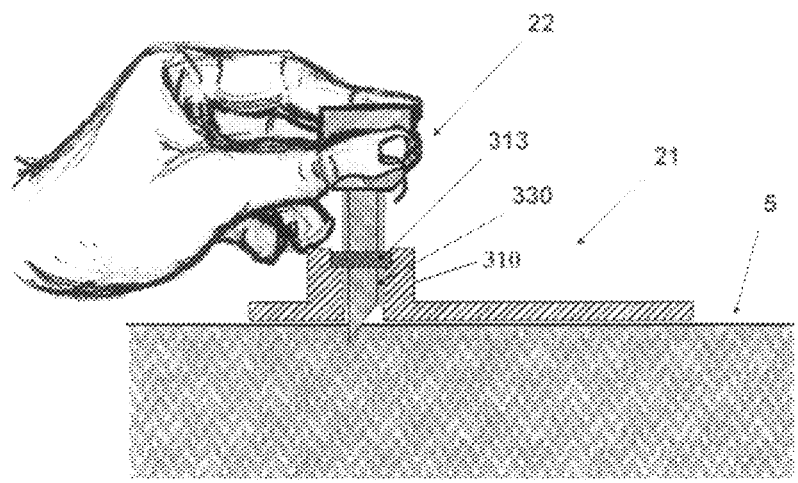
Figure 13D:
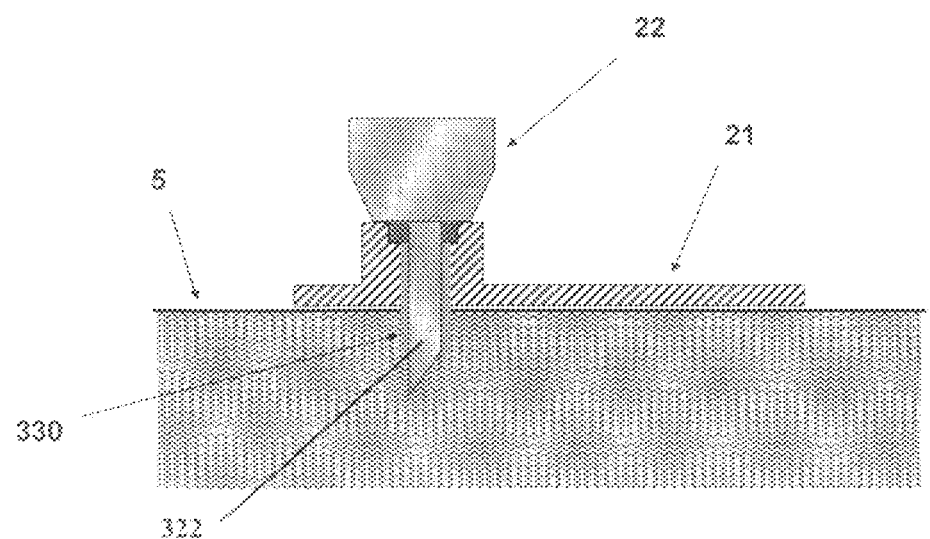

FIG. 13A shows the two parts before insertion. The cradle part (21) comprises cradle base (300) and well portion (310). The penetration cartridge part (22) comprises cannula (330), penetrating member (320) and septum (313). FIG. 13B shows the cradle part (21) after it has been attached to the patient skin (5). The attachment can be done by adhesives or by other means known in the art. FIG. 13C shows manual insertion of the penetration cartridge (22) through the well portion (310). The septum (313) is pierced by the dagger (321). FIG. 13D shows sharp tip of the dagger (322) and the cannula (330) within the subcutaneous tissue.

Figure 13E:
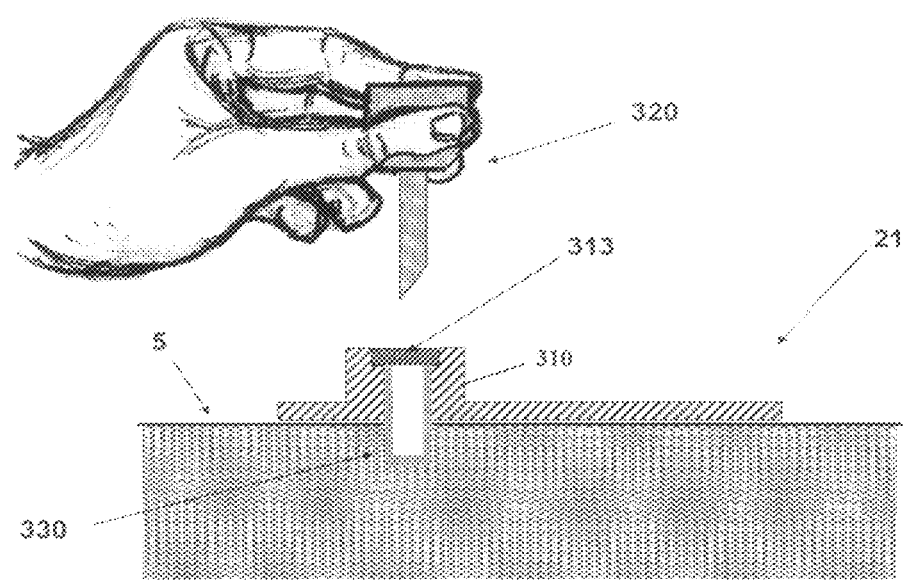
Figure 13F:
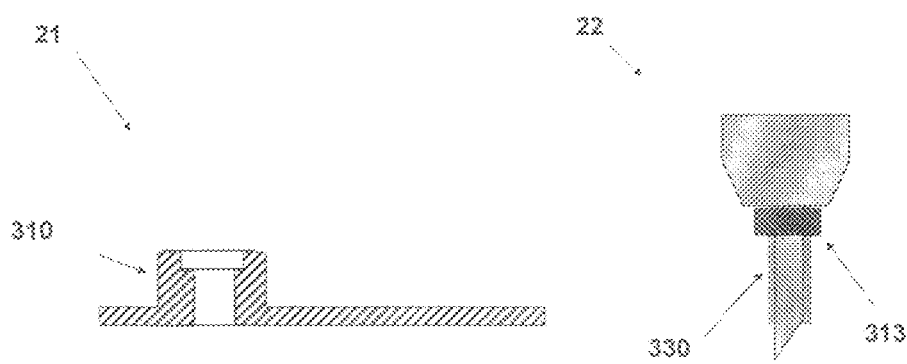
Figure 13G:
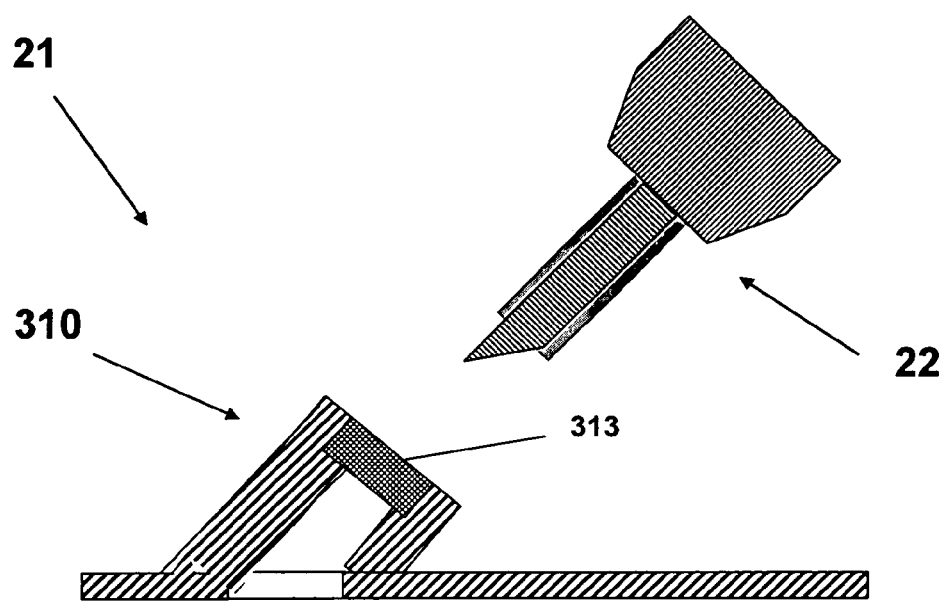

FIG. 13E shows the removal of the penetrating member (320). The cradle part (21) remains adhered to the skin and the cannula (330) remains in the body. The self-sealable septum (313) of the well portion (310) prevents leaking of the therapeutic fluid as well as contamination. FIG. 13F shows another embodiment of the penetration cartridge part (22). In this embodiment the septum (313) is attached to the cannula (330) and is introduced into the upper side of the well portion (310) during insertion of the penetrating cartridge (22) through the well portion (310). FIG. 13G shows another embodiment of the cradle part (20). In this embodiment the well portion (310) is in a tilted position allowing the insertion of the penetrating cartridge part (22) at an angle with respect to the skin.

Figures 14A, 14B:
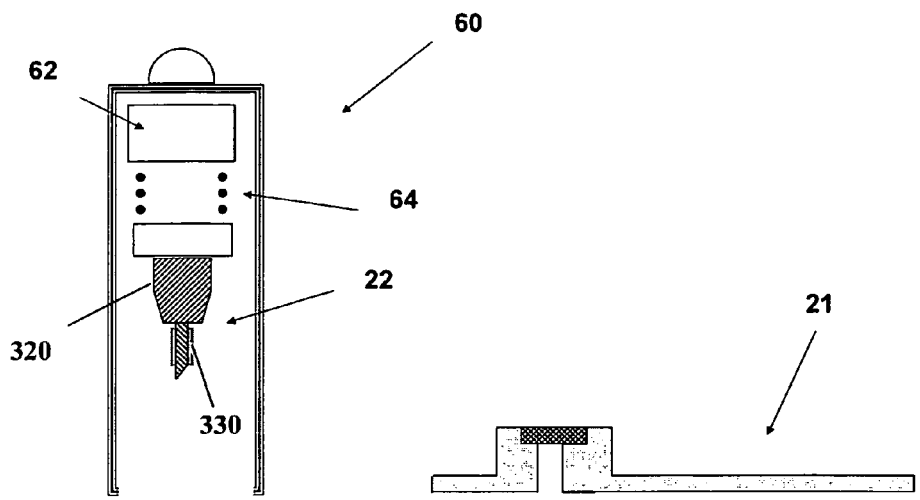
FIG. 14*a-f* are cross-sectional schematic views of an inserter used for cradle and cannula placement, where the needle unit comprises a cradle part and a penetrating cartridge part.
Figure 14C:
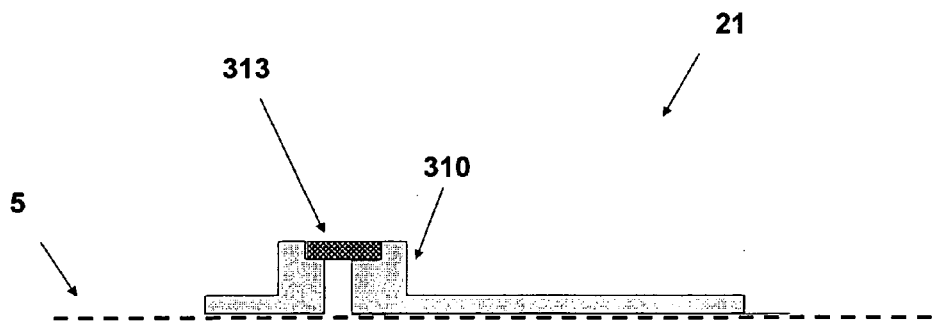
Figure 14D:
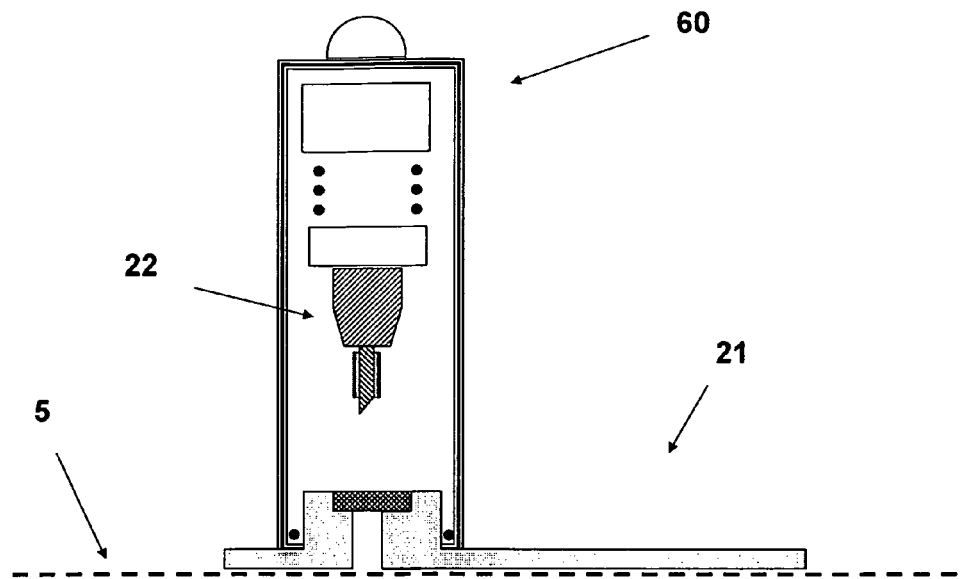
Figure 14E:
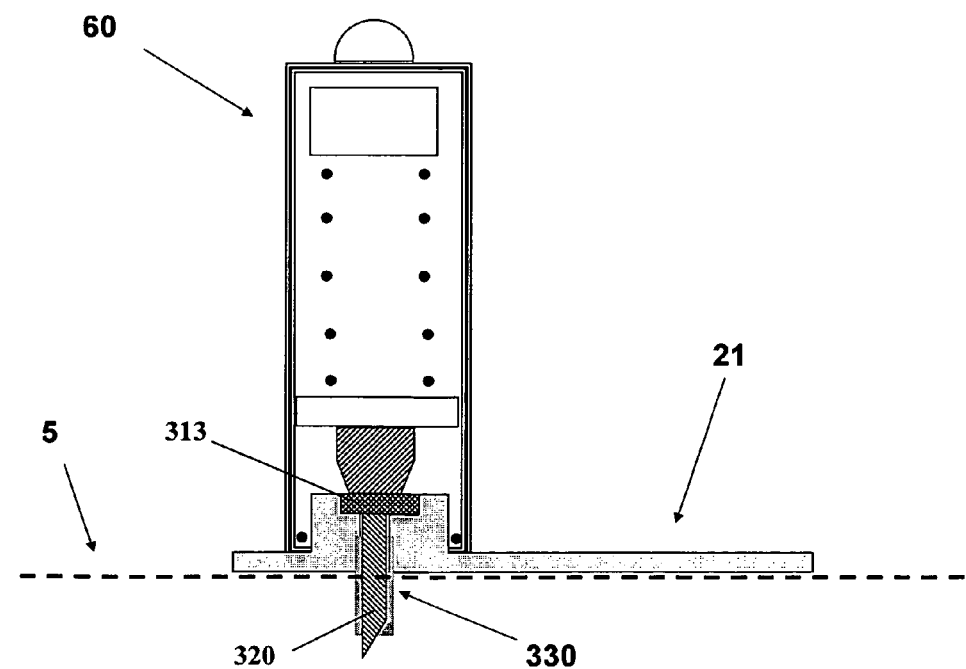
Figure 14F:
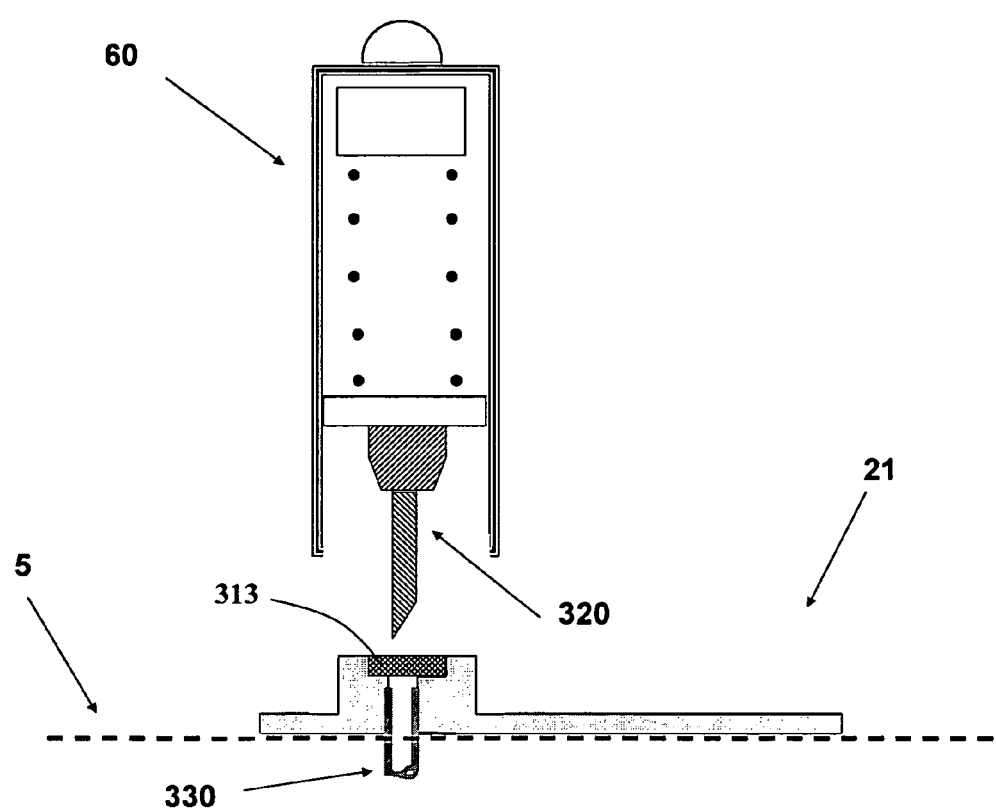

FIGS. 14A-14F show another embodiment of an inserter for use with a two part needle unit. The inserter (60) is used for the insertion of the cartridge part (22) into the cradle base part (21). In this embodiment the cradle part (21) is first manually attached to the skin (5) and consecutively the penetrating cartridge part (22) is automatically inserted by the inserter (60). FIG. 14A shows the inserter housing (60) and the penetrating cartridge part (22) before insertion. FIG. 14B shows the cradle part (21). The inserter housing (60) accommodates actuation mechanism (62), spring-loaded plunger element (64) and the penetration cartridge part (22). The penetrating cartridge part (22) comprises cannula (330) and penetrating member (320). The cradle part (21) comprises cradle (300) and well portion (310). FIG. 14C shows the cradle part (21) attached to the patient skin (5). The attachment can be done by adhesives or by other means known in the art. FIG. 14D shows the inserter housing (60) put on the well portion (330) of the cradle part (21). FIG. 14E shows the penetrating cartridge (22) after penetrating the skin (5) such that the cannula (330) has penetrated within the subcutaneous tissue. FIG. 14F shows the removal of the penetrating member (320). The cradle part (21) remains adhered to the skin (5) and the cannula (330) remains in the body.

Figure 15:
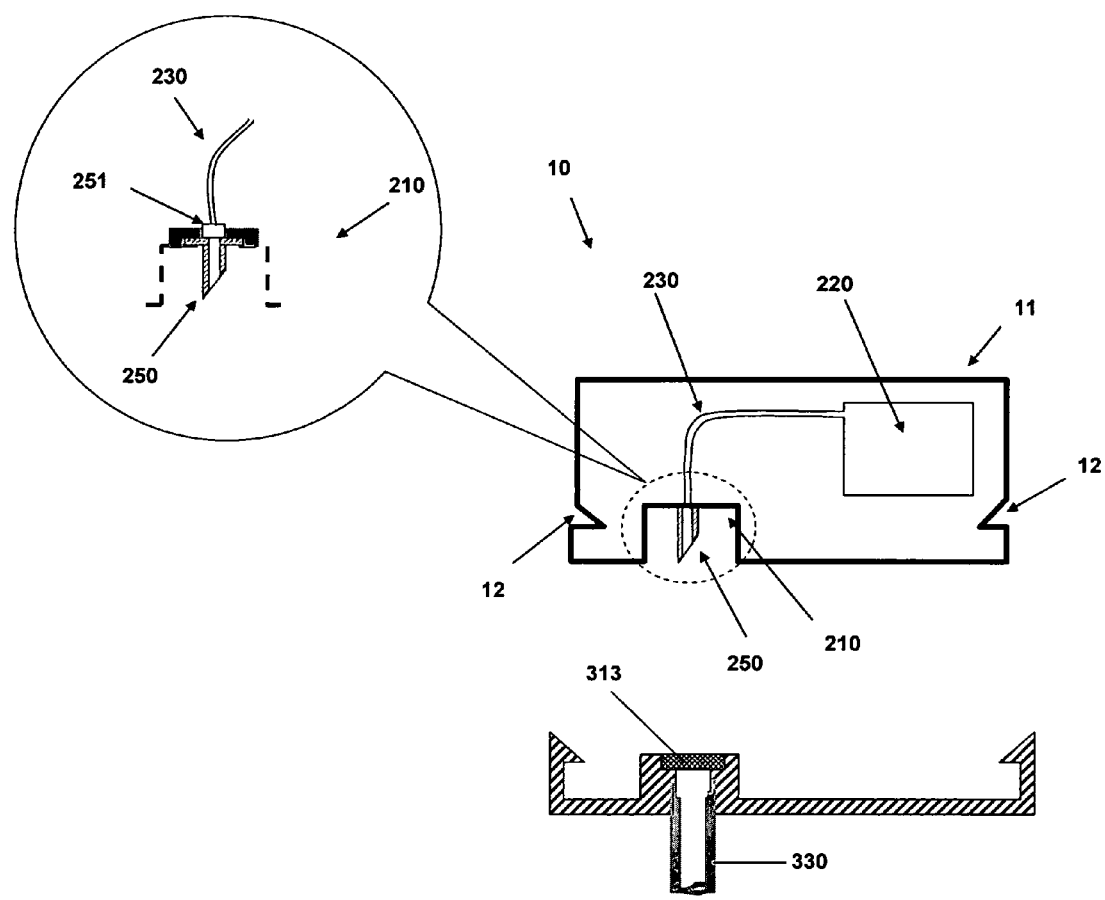
FIG. 15 is a schematic cross-sectional view of a single-part patch unit.

FIG. 15 shows still another embodiment of the patch unit (10) that is composed of a single part. The patch unit (10) contains housing (11), which is provided with exit port (210), through which protrudes a short connecting lumen (250) having sharpened forward end. The opposite rear end of the lumen is in fluid communication with the delivery tube (230) and reservoir (220). When the patch unit (10) is attached to the needle unit (20) the sharpened end of the lumen (250) enters in the cannula (330) to provide fluid communication between the cannula (330) and reservoir (220). The connecting lumen (250) is rigidly secured within the exit port (210). It is connected by its rear end to the tube (230) through a connector (251). The housing (11) is provided with lateral notches (12). When the patch unit (10) is attached to the needle unit (20) the sharpened forward end of the connecting lumen (250) pierces the septum (313) of the needle unit (20) and enters in the cannula (330). By virtue of this provision fluid communication is provided between reservoir (220) and cannula (330). The lateral notches (12) allow connecting of the patch unit (10) to the needle unit (20).

Figure 16:
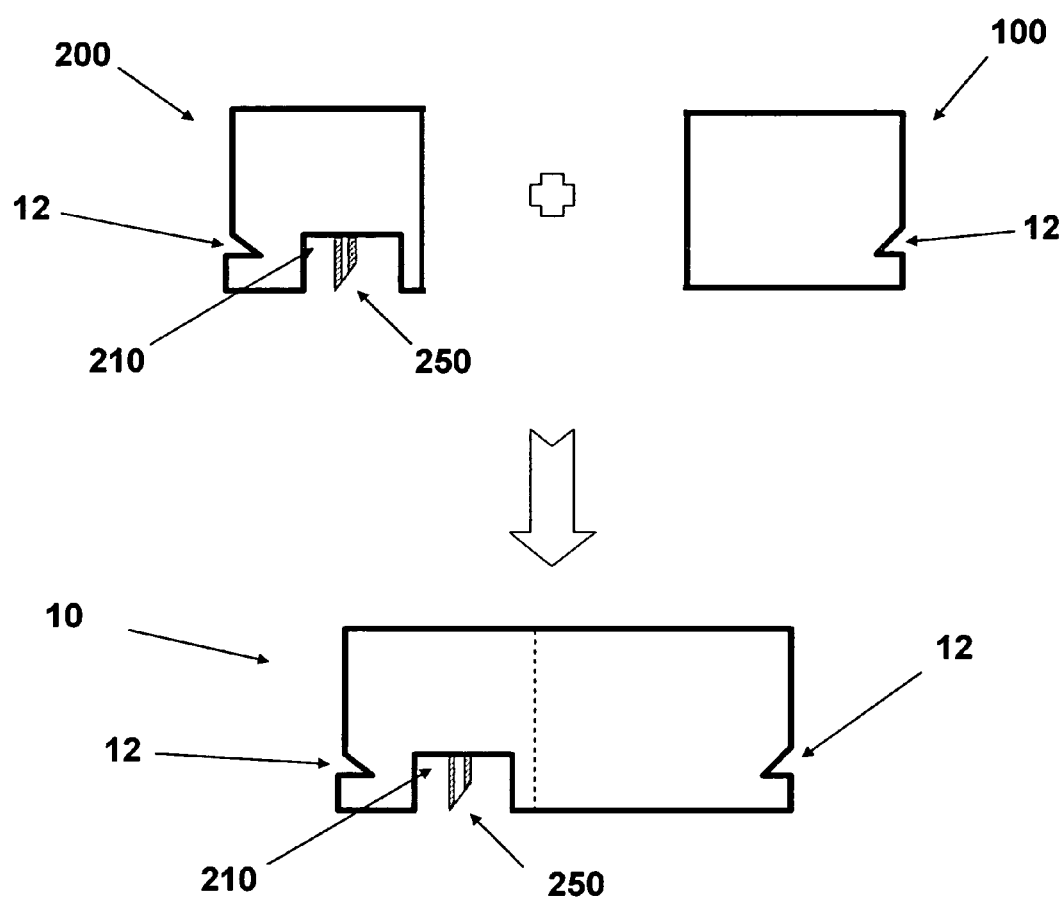
FIG. 16 is a schematic cross-sectional view of a two-part patch unit.

FIG. 16 shows another embodiment of the patch unit (10) composed of two parts. A reusable part (100) contains components that can be used multiple times while disposable part (200) contains disposable components including reservoir (220) and exit port (210). The disposable components are used until emptying of the reservoir (220). The connecting element (e.g., connecting lumen) (250) emerges from the exit port (210) in the disposable part (200). Lateral notches (12) are provided on exterior sides of both parts. Before connecting the patch unit (10) with the needle unit (20) the disposable (200) and reusable (100) parts are attached to each other and constitute the single patch unit (10) as seen in FIG. 16.

Figure 17A:
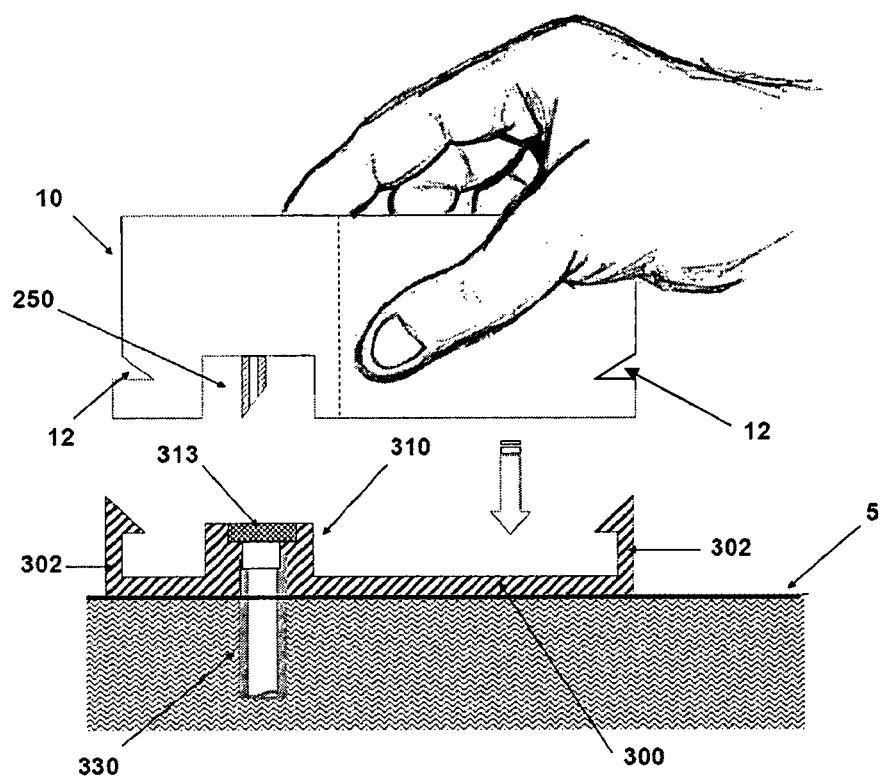
FIG. 17*a-f* are transverse cross-sectional views depicting connection of the patch unit to and disconnection of the patch unit from the needle unit.
Figure 17B:
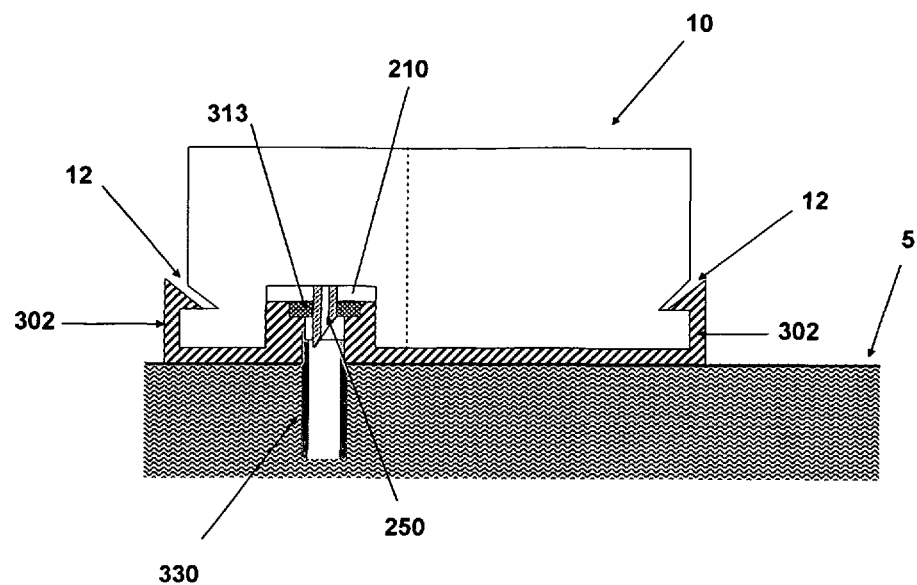

FIGS. 17A-17F show an example of connection and disconnection of the patch unit (10) and the needle unit (20). FIG. 17A shows the two units before connection. The needle unit (20) is attached to the user skin (5) and the cannula (330) penetrates within the subcutaneous tissue. The patch unit (10) in this example is composed of two parts and contains lateral notches (12), exit port (210) and connecting lumen (250). The needle unit (20) contains cradle (300), cannula (330), anchoring latches (302), well portion (310) and well septum (313). When the patch unit (10) is brought into contact with the needle unit (20) it is guided by the anchoring latches (302) maintaining precise alignment between the two units and anchoring of the two units. FIG. 17B shows the patch unit (10) after is has been connected to the skin-adhered needle unit (20) and secured due to snapping engagement of the anchoring latches (302) provided at the outside periphery of the needle unit (20) with the lateral notches (12) provided at the patch unit (10).

Figure 17C:
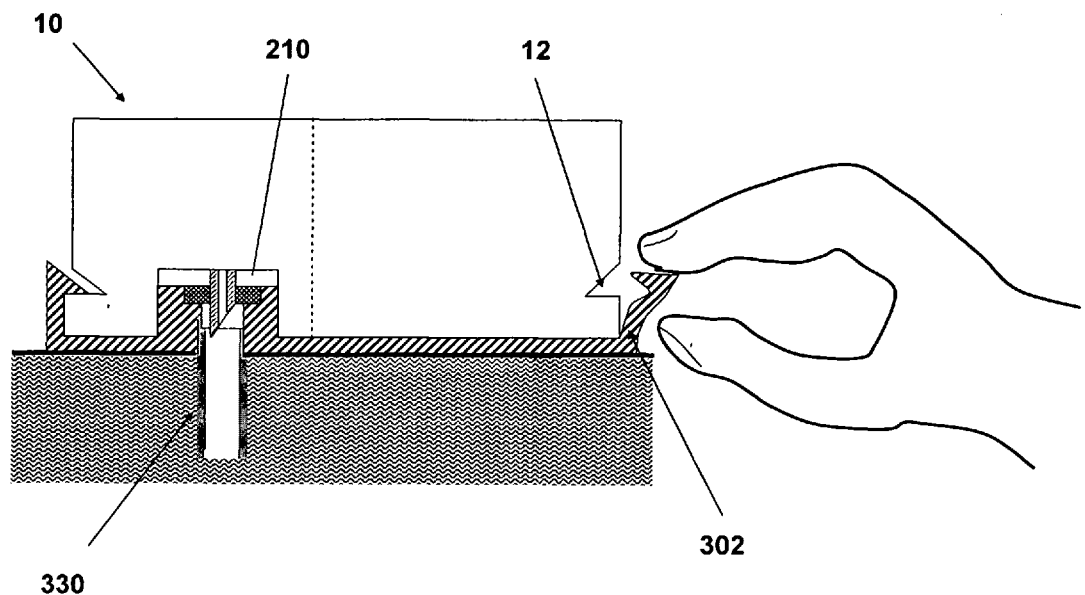
Figure 17D:
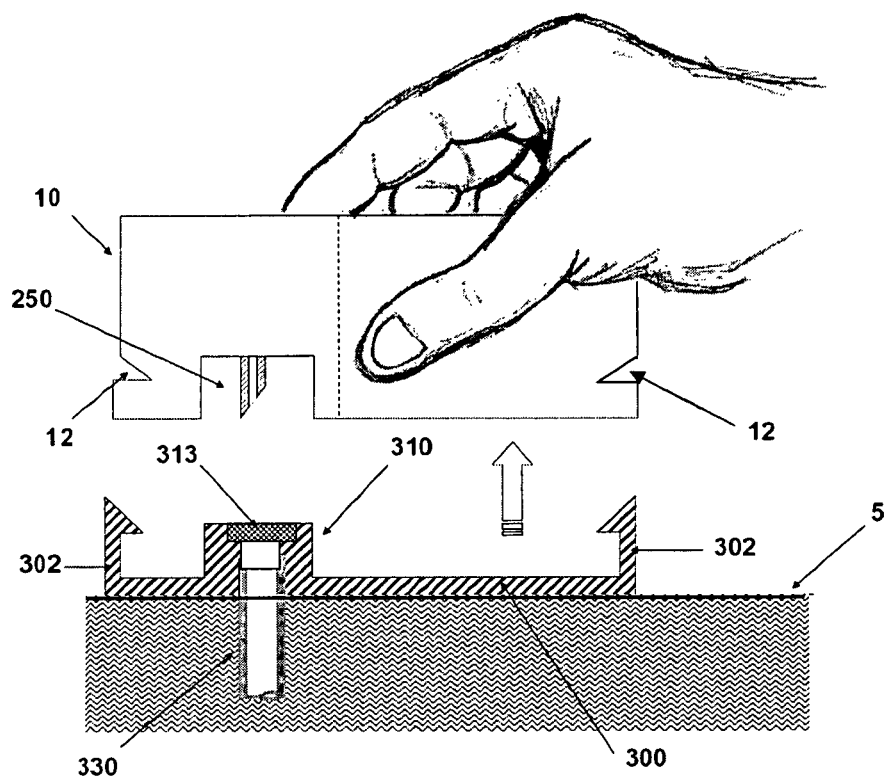
Figure 17E:
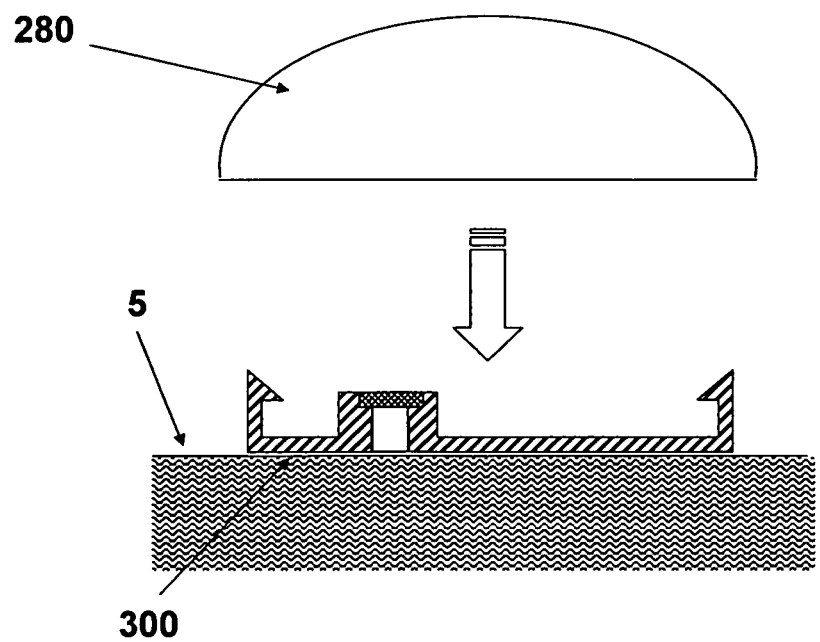
Figure 17F:
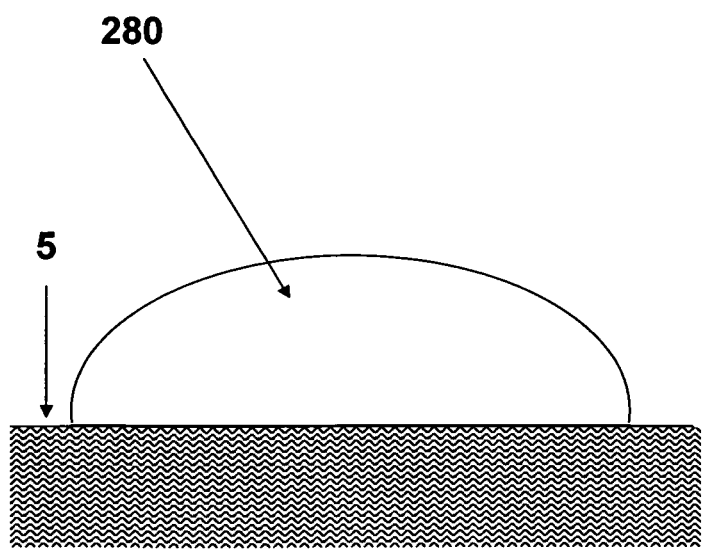

The sharpened end of the connecting lumen (250) pierces the septum (313) thus allowing fluid supply to the well portion (310) and then to the cannula (330). FIG. 17C shows the patch unit (10) being disconnected by back-pulling the elastically deformable latches (302). FIG. 17D shows the patch unit (10) disconnected from the needle unit (20) which remains adhered to the skin (5) and the cannula (330) remains in the body. The self-sealable septum (313) prevents body fluids from leaking and also prevents contamination. When the patch unit (10) is disconnected, the cradle (300) could be protected to avoid contamination and abrasion of protruding elements by a protective cover (280), as shown in FIGS. 17E-17F.

The protective cover (280) can be configured as a convex-shaped rigid polymeric cover which conceals the cradle (300) within. Thus, the cradle (300) when covered is not exposed to the environment. The protective cover (280) should be removed before reconnection of the patch unit (10).

Figure 18A:
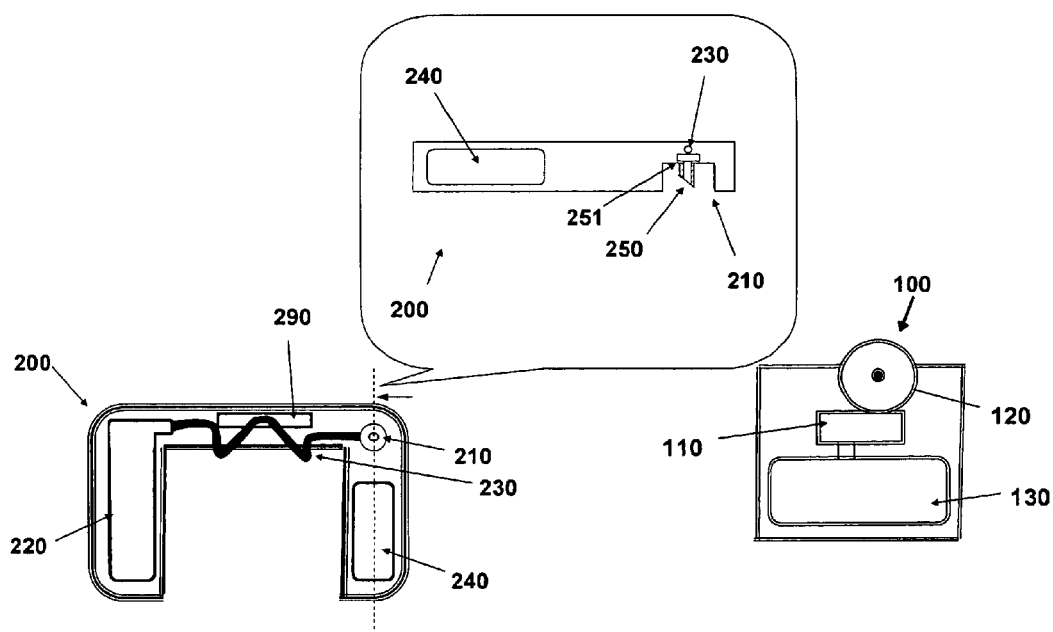
FIG. 18*a-k* are views of an embodiment of a patch unit comprising a reusable and a disposable part. The figures depict matching and priming as well as adherence of the cradle, connection and disconnection of the patch unit.

FIGS. 18A-18K shows another embodiment of a fluid delivery device that includes a patch unit and a needle unit. In this embodiment the patch unit (10) comprises two parts—reusable part (100) and disposable part (200). The disposable part is provided with the exit port (210) which is located not in the center of the disposable part (200) but close to its lateral side. FIG. 18A shows the two parts. The disposable part (200) has a U-shape configuration and the reusable part (100) has a squared configuration mating the recess in the U-shaped disposable part (200). The reusable part (100) is fitted with driving mechanism (110), with pumping mechanism (120) e.g. a peristaltic pump and with suitable electronics (130). The disposable part (200) is fitted with reservoir (220), with power supply means (240), with delivery tube (230) and with connecting lumen (250). The tube (230) is connected by its one end to the reservoir (220) and by its opposite end to the connecting lumen (250). The connecting lumen (250) resides within the exit port (210).

Figures 18B, 18C:
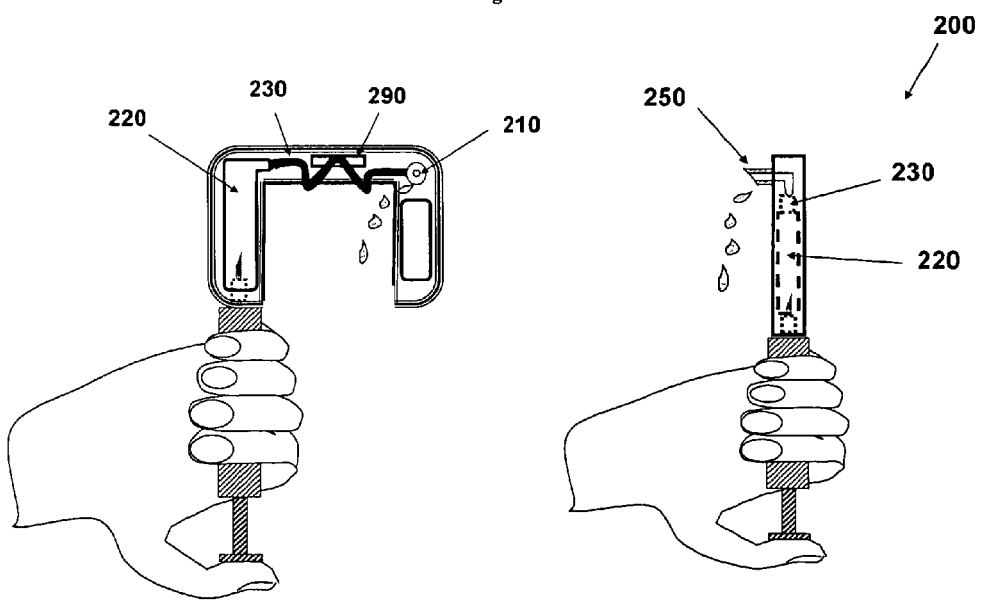
Figure 18D:
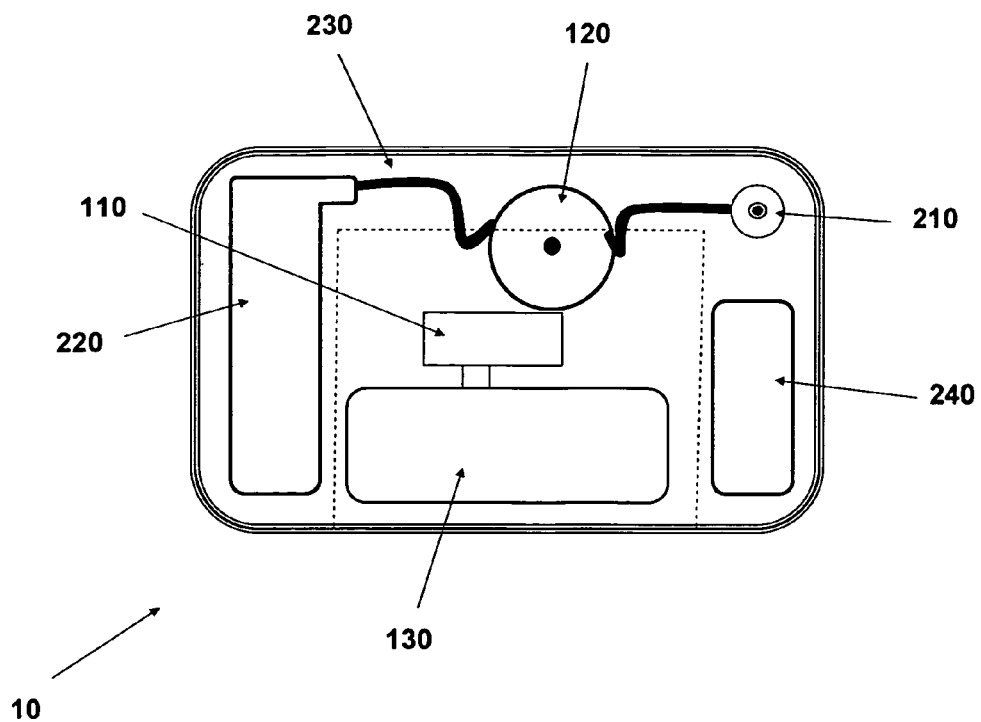
Figure 18E:
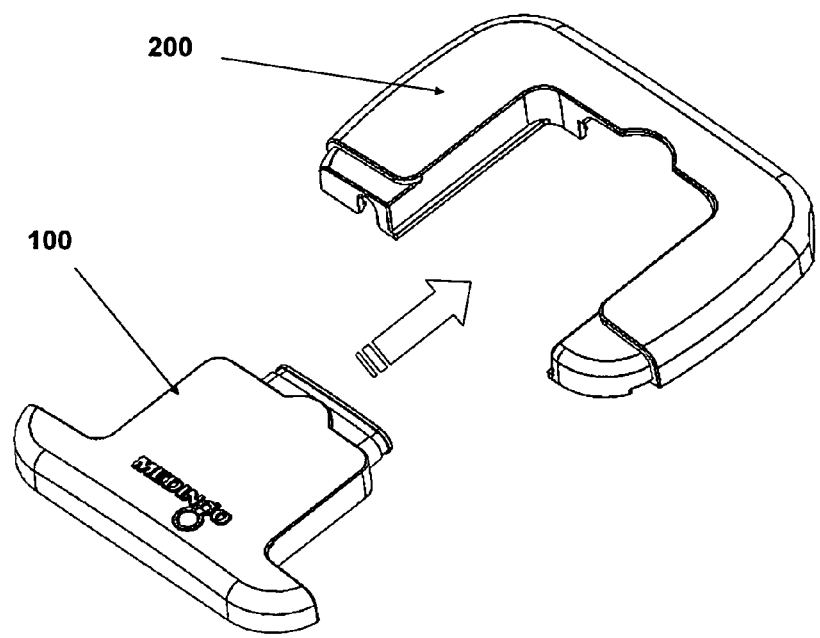
Figure 18F:
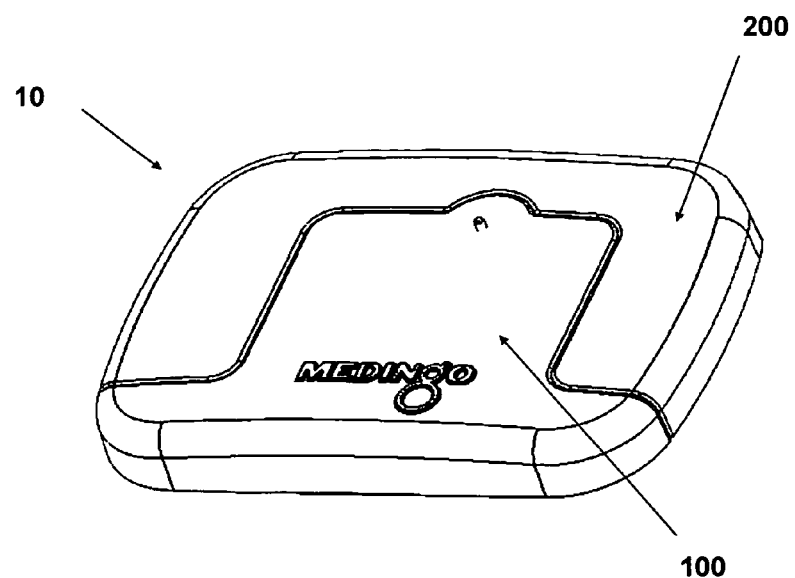
Figure 18G:
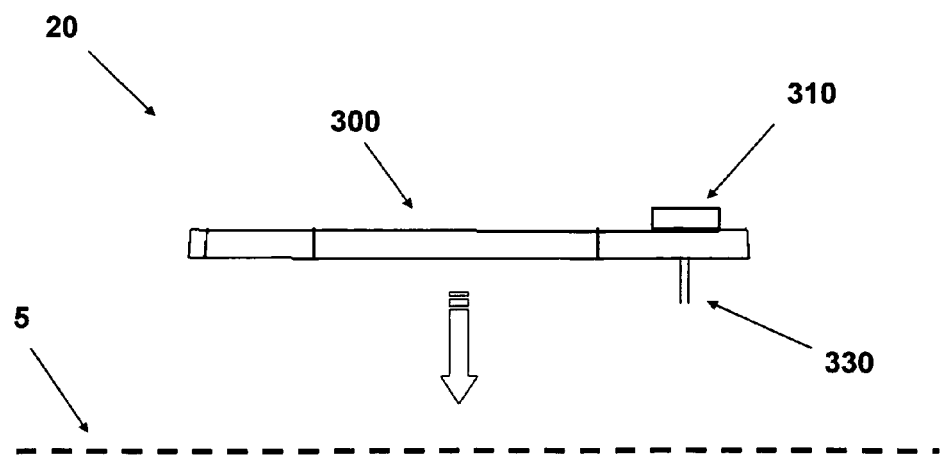
Figure 18H:
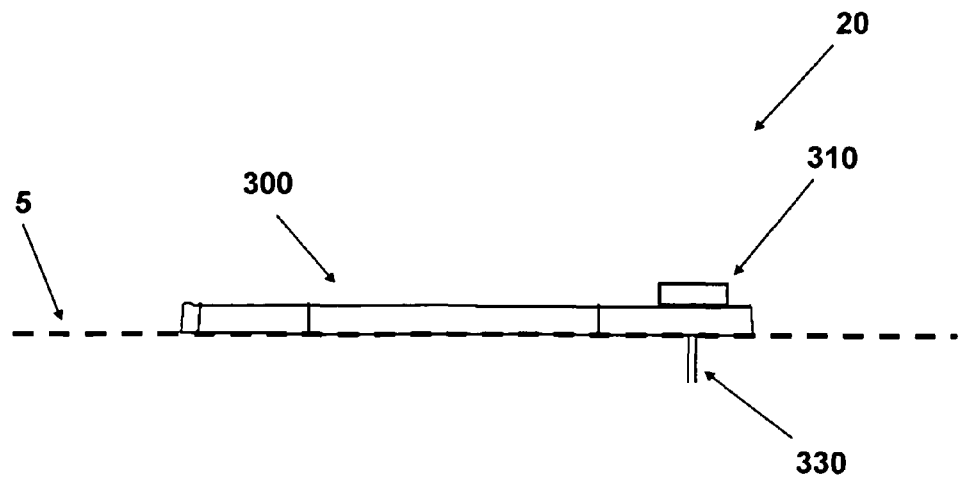
Figure 18I:
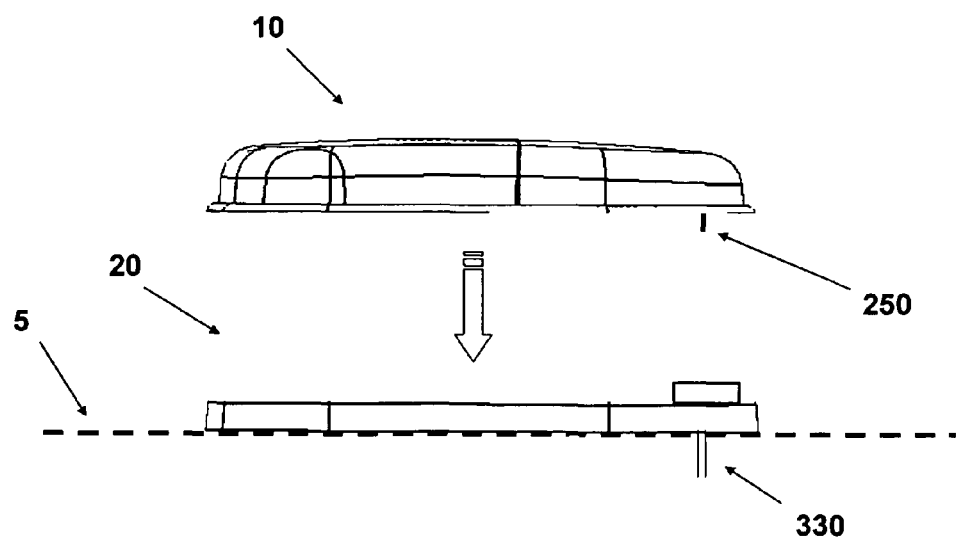
Figure 18J:
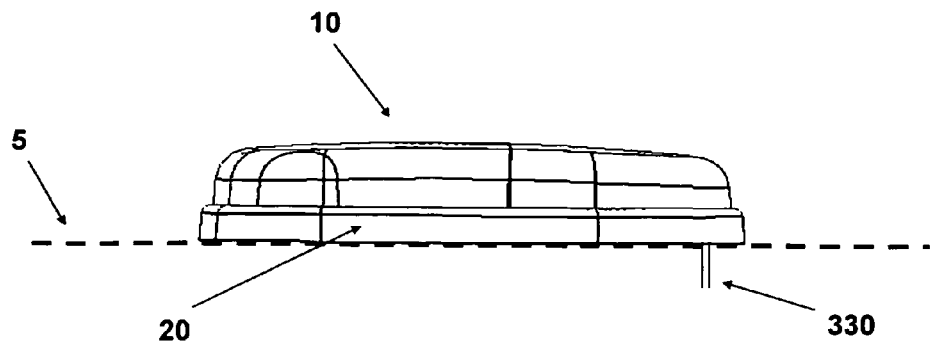
Figure 18K:
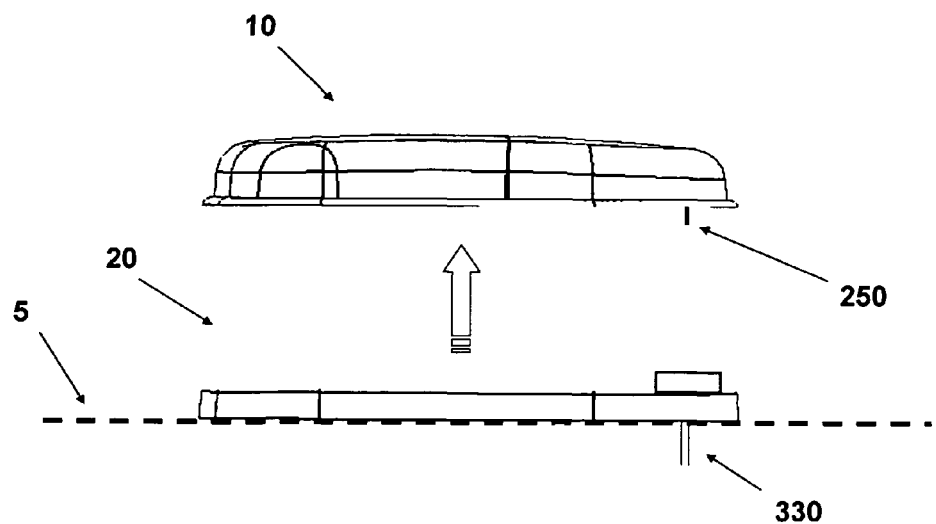

With reference to FIGS. 18B and 18C it is shown how reservoir (220) is being filled and priming is carried out. In these figures it is shown that the filling and the priming are carried out by a syringe connectable to the reservoir (220). Connection of the syringe to the reservoir may be also carried out by means of a dedicated adapter, examples of which are described in more detail in commonly owned application U.S. Ser. No. 60/838,660, which is hereby incorporated by reference. The adapter allows connection of the filling syringe to the reservoir (220). FIG. 18D shows the patch unit (10) assembled after the reusable part (100) and the disposable part (200) are connected. Upon connection, air is purged out of the reservoir (220), out of the tube (230) and out of the connecting lumen (250). FIG. 18E shows the reusable part (100) and the disposable part (200) before they are connected. FIG. 18F shows another view of the patch unit (10) after connecting the two parts. FIG. 18G shows the needle unit (20) before its adherence to the skin. The needle unit (20) comprises cradle (300), well portion (310) and cannula (330). FIG. 18H shows the needle unit (20) after it has been adhered to skin (5). FIG. 18I shows connection of patch unit (10) to needle unit (20); FIG. 18J shows both units being connected (operation mode) and FIG. 18K shows the units being disconnected.

Figure 19A:
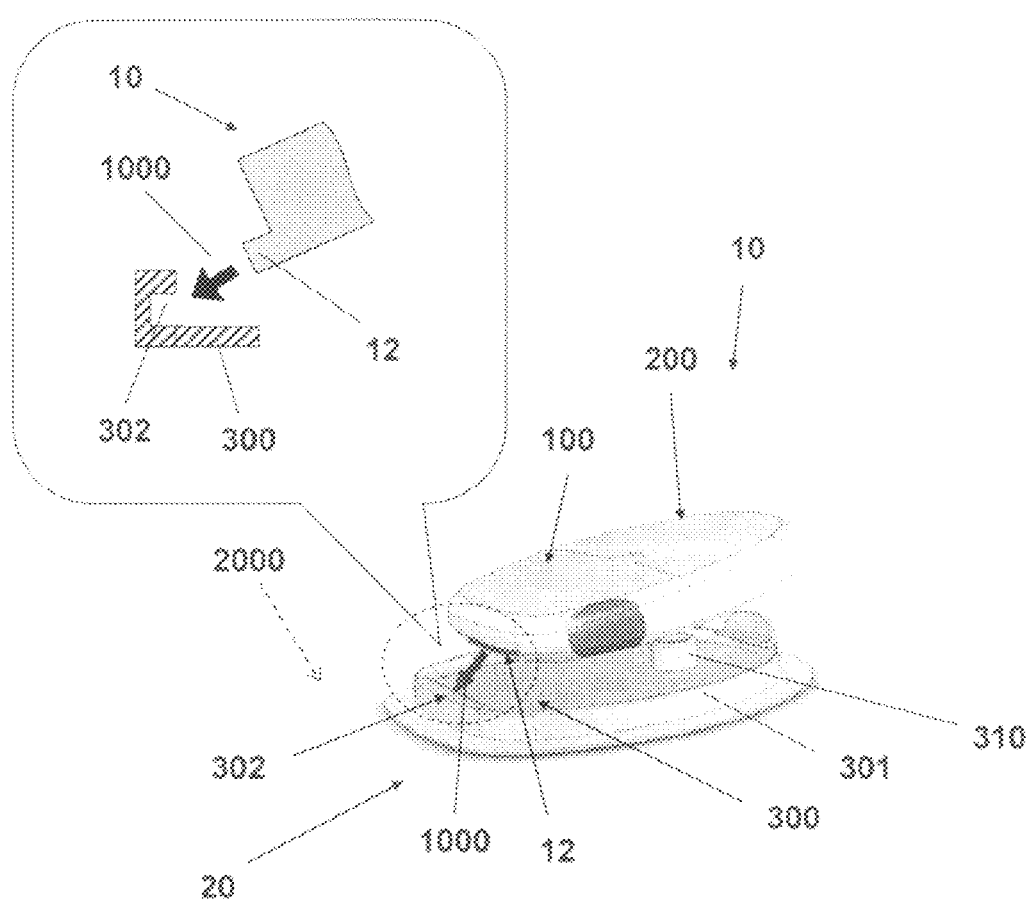
FIG. 19*a-d* are views of an embodiment of the patch unit and needle unit employing rear and front latches for connection and disconnection.

FIGS. 19A-19D show another embodiment of a fluid delivery device and a method for connecting a patch unit (10) and a needle unit (20). The patch unit (10) comprises a reusable part (100) and a disposable part (200). The needle unit (20) comprises a cradle (300) having an elevated peripheral wall (301), well portion (310) and adhesive layer at the lower surface of the cradle. FIG. 19A shows the first step of connecting the patch unit (10) to the needle unit (20) by moving the patch unit (10) towards the needle unit (20) along arrow (1000), such that a protrusion (12) in the patch unit (10) engages with a corresponding recess (302) provided on the rear end (2000) of the cradle (300) (or vice versa).

Figure 19B:
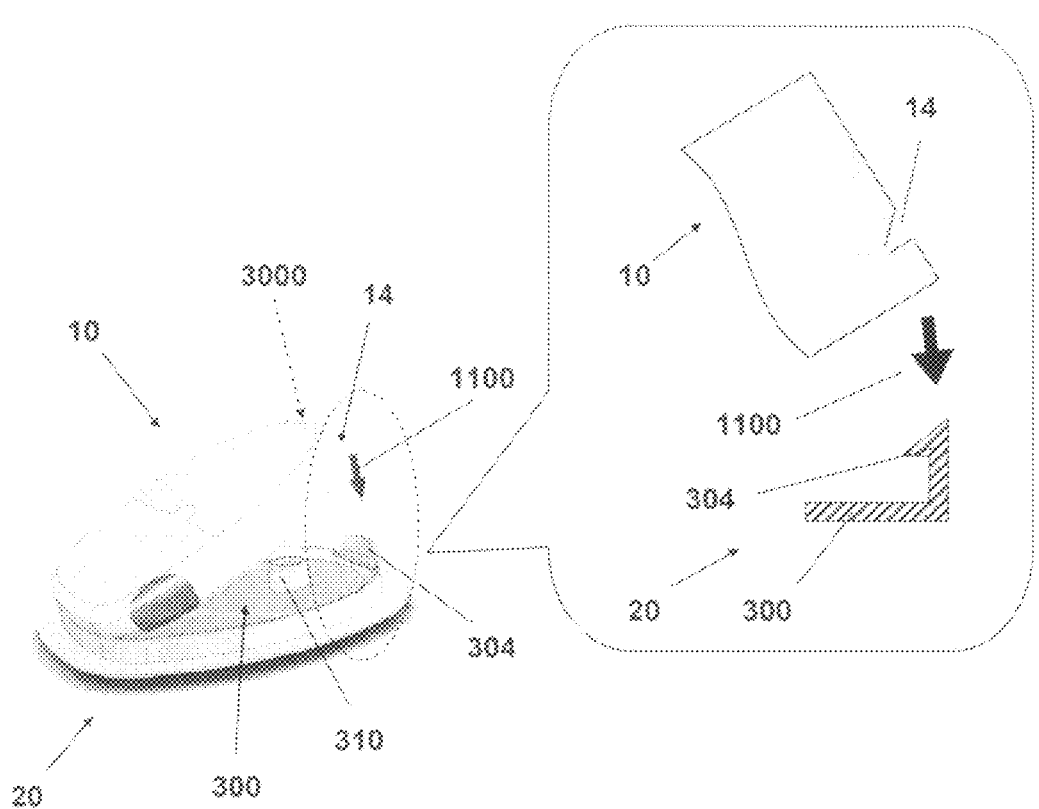
Figure 19C:
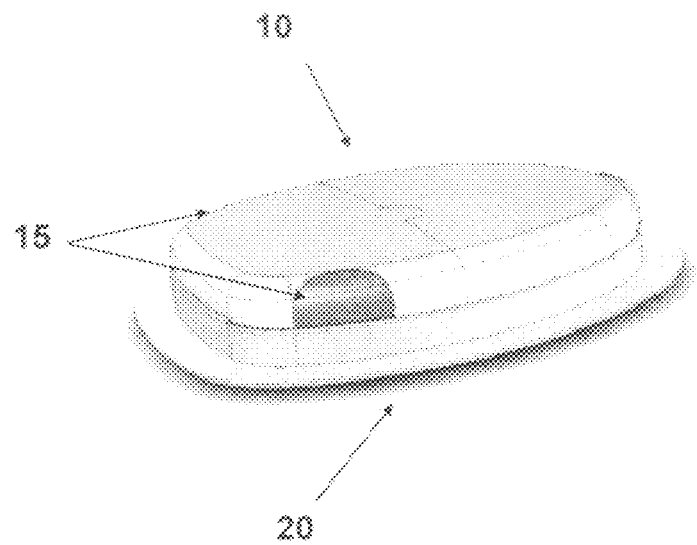
Figure 19D:
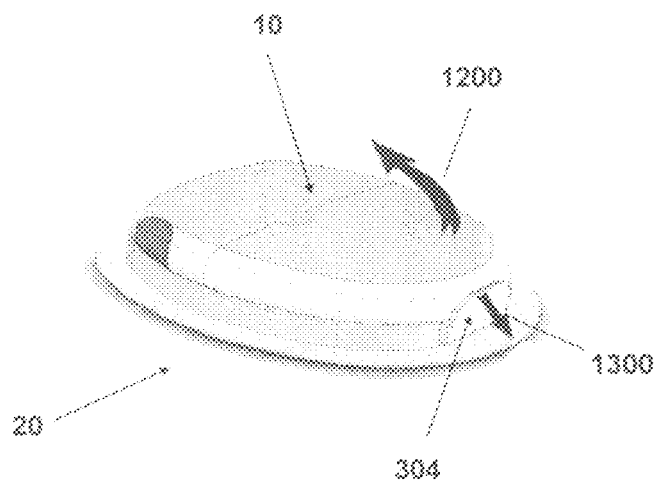

FIG. 19B shows the next step of connecting the two units by pivoting the front end (3000) of the patch unit (10) towards the needle unit (20) along arrow (1100). The connection is carried out by snapping engagement of a latch (304) in the cradle (300) with a corresponding notch (14) in the patch (10). FIG. 19C shows the device in an operation mode after the patch (10) and the needle (20) units have been connected. In this configuration the patient can conveniently use the device since connecting and disconnecting of the patch unit (10) and the needle unit (20) does not affect the use of the device. The patient can give an insulin bolus dose by pressing simultaneously the two buttons/switches (15) provided at the lateral walls of the reusable part (100). FIG. 19D shows disconnection of the units by the release of a latch (304), pulled along the arrow (1300). The patch unit (10) now may be withdrawn by pivoting it along the arrow (1200).

Figure 20A:
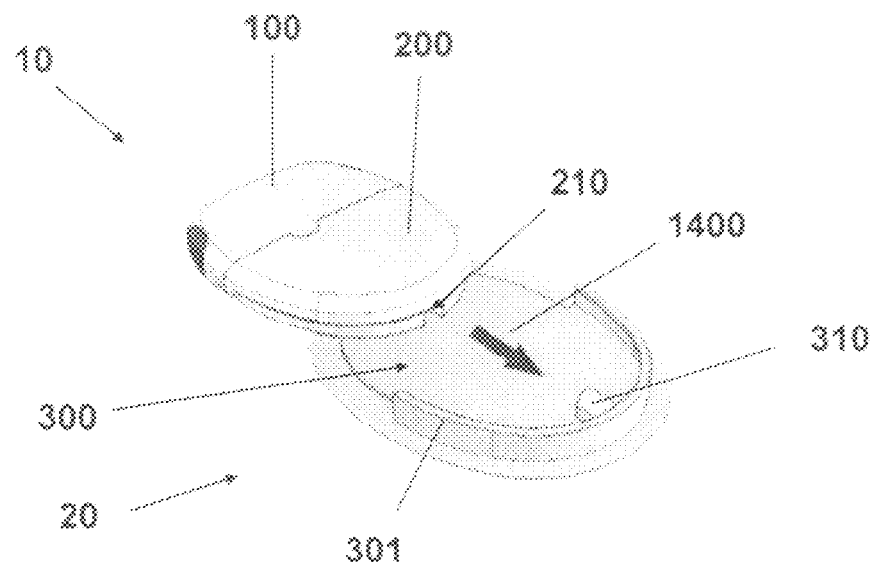
FIG. 20*a-e* are views of an alternative embodiment of the patch unit and needle unit depicting slide connection and disconnection.

FIGS. 20A-20D shows another embodiment of a fluid delivery device and a method for connection the patch unit (10) and the needle unit (20). The patch unit (10) comprises a reusable part (100) and a disposable part (200). There is provided an exit port (210) in the disposable part (200). The needle unit (20) comprises a cradle (300) having an elevated side wall (301), a well portion (310) and adhesive layer at the lower surface of the cradle. FIG. 20A shows patch unit (10) and needle unit (20) being connected by a sliding movement of the patch unit (10) towards the cradle (300) along arrow (1400).

Figure 20B:
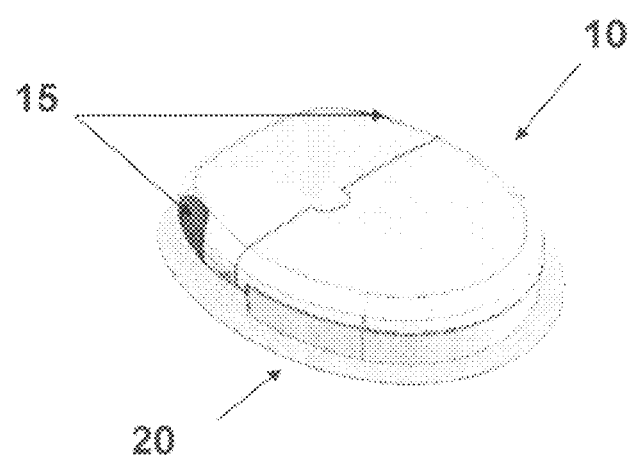

FIG. 20B shows operation mode of the device after the patch unit (10) has been connected to the needle unit (20). Patient can control insulin bolus dose by using the remote controller or by pressing simultaneously on the two buttons/switches (15).

Figure 20C:
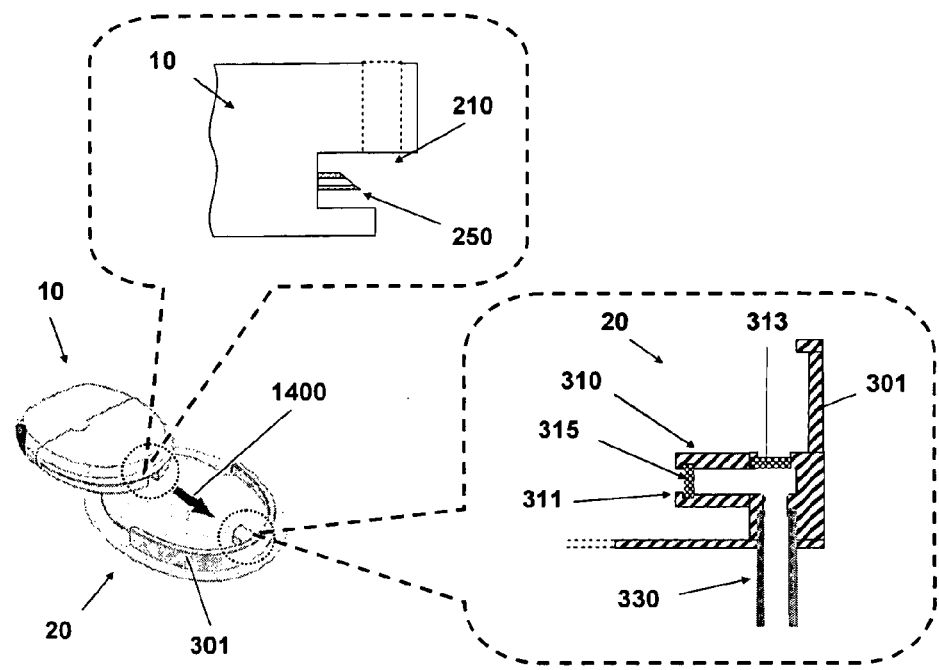

FIG. 20C shows the connection of the exit port (210) with well portion (310) therefrom introducing the connecting lumen (250) into the well portion (310). Connection by sliding requires horizontally directed connecting lumen (250) on the patch unit (10) and a lateral inlet port (311) on the well portion (310). The self-sealable septum (313) is provided for the penetrating member insertion. This septum (313) seals the well portion (310) and it is oriented horizontally. There is provided also an additional self-sealable septum (315) which is directed vertically. This septum is provided for penetrating of the connecting lumen (250).

Figure 20D:
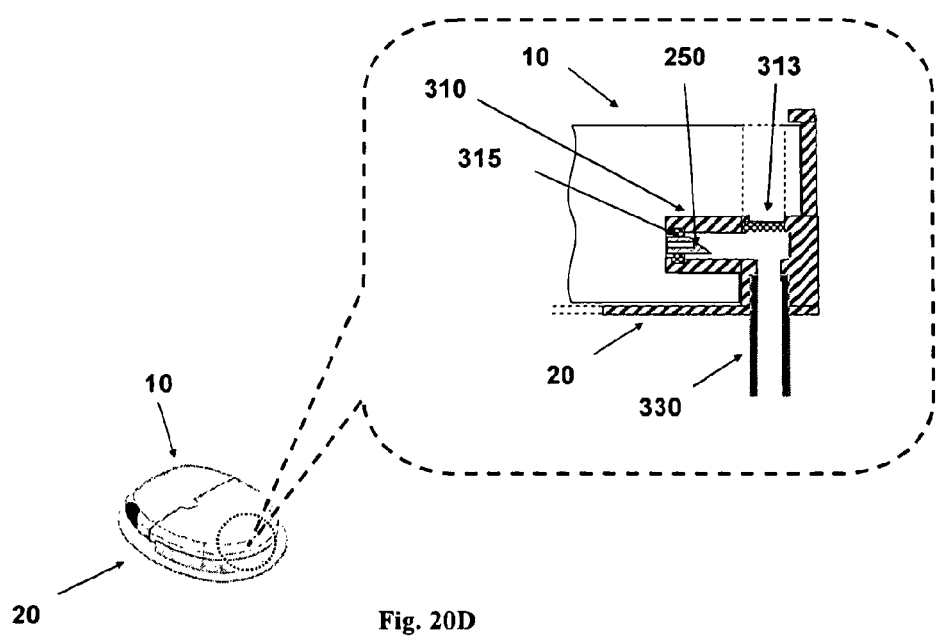
Figure 20E:
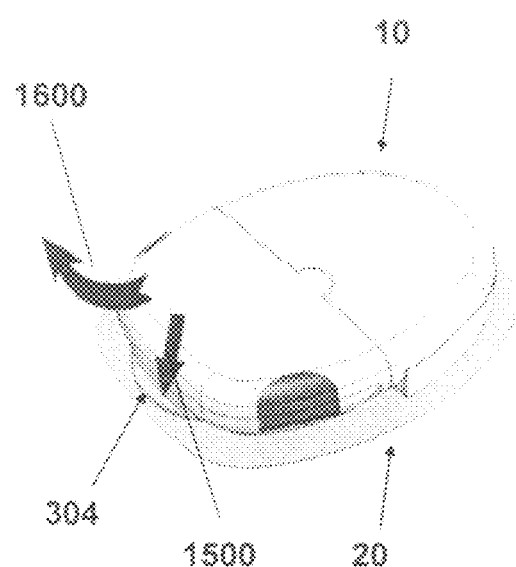

FIG. 20D shows the connecting lumen (250) which pierces the well's septum (315) allowing fluid communication with the reservoir. FIG. 20E, shows disconnection of patch unit (10) from needle unit (20) by releasing the latch (304) along arrow (1500) followed by the sliding withdrawal of the patch unit (10) along arrow (1600).

Figure 21A:
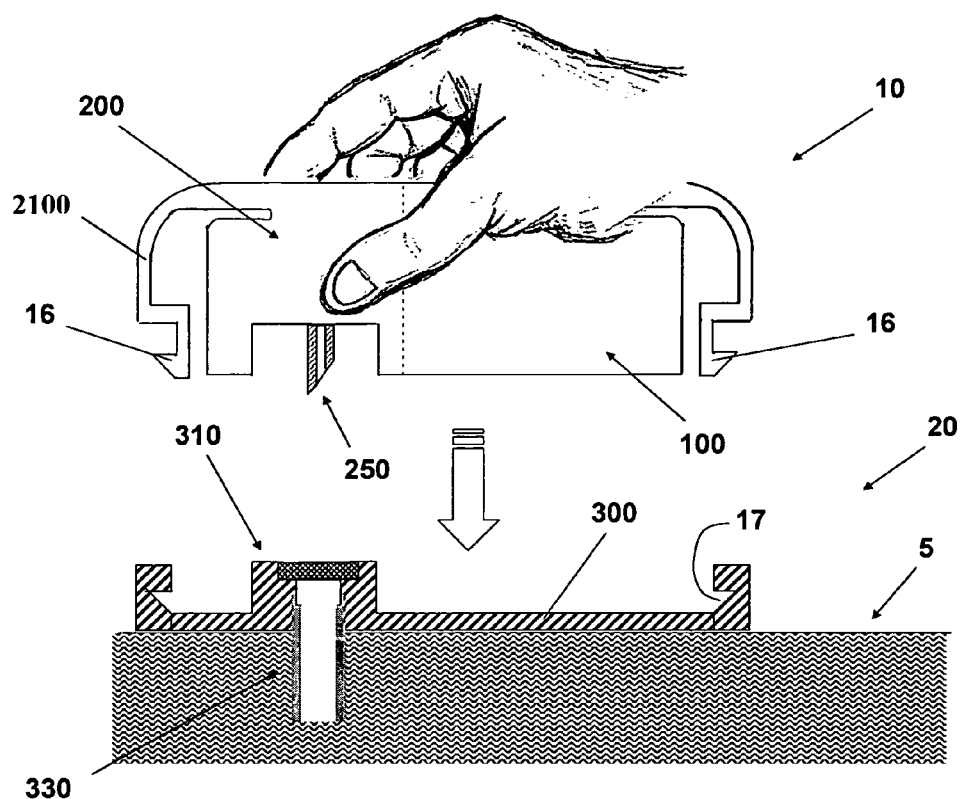
FIG. 21*a-c* are transverse cross sectional views of an alternative embodiment of the patch unit and needle unit depicting connection and disconnection by virtue of flexible latches.
Figure 21B:
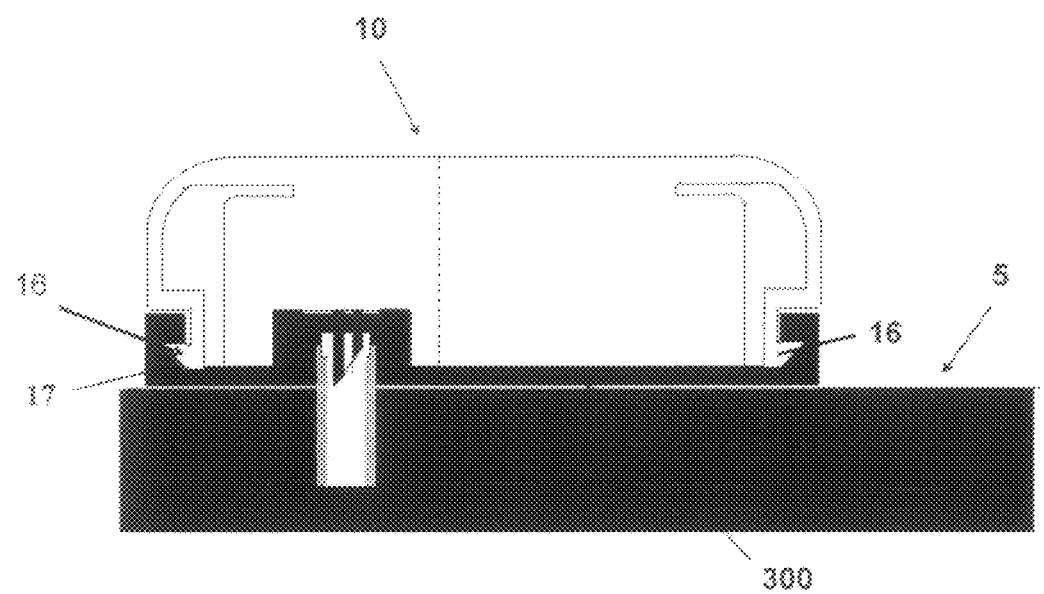
Figure 21C:
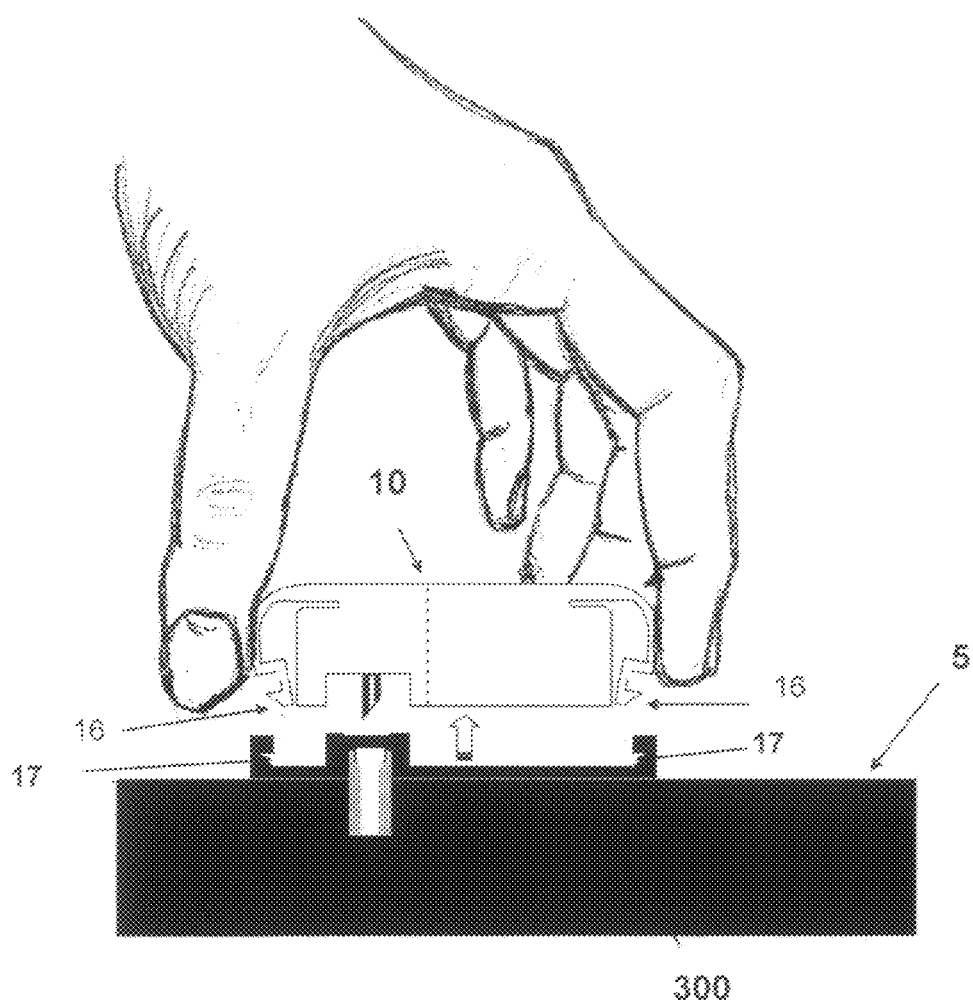

FIGS. 21A-21C show another embodiment of a fluid delivery device and a method for connecting a patch unit (10) and a needle unit (20). The patch unit (10) comprises a reusable part (100) and a disposable part (200). The patch unit (10) is provided with elastically deformable latches (16) provided at the periphery of the patch unit (10). The needle unit (20) comprises a cradle (300) and a well portion (310). Notches (17) are provided at the periphery of the cradle (300). The notches (17) are configured to mate the latches (16), such that snapping engagement is possible therebetween. The peripheral wall (2100) of the patch unit (10) is elastically deformable, such that latches (16) can be easily pressed inwardly. FIG. 21A shows the two units are being brought together and are about to be connected by virtue of snapping engagement of latches (16) with notches (17). FIG. 21B shows patch unit (10) secured on the cradle (300) by virtue of snapping of the latches (16) on notches (17). FIG. 21C shows disconnection of patch unit (10) by squeezing the wall of the patch unit (10) such that latches (16) are elastically displaced inwardly to allow their disengagement from the notches (17).

Figure 22A:
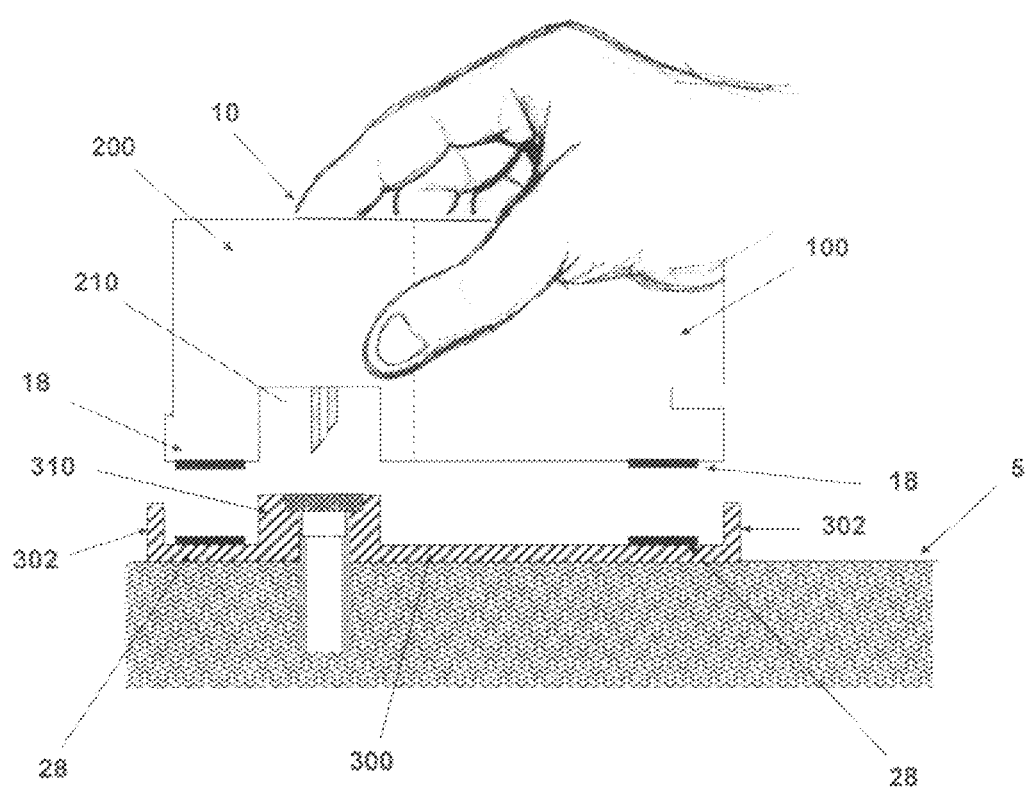
FIG. 22*a-c* are transverse cross-sectional views of an alternative embodiment of the patch unit and needle unit depicting connection and disconnection by virtue of magnetic forces.
Figure 22B:
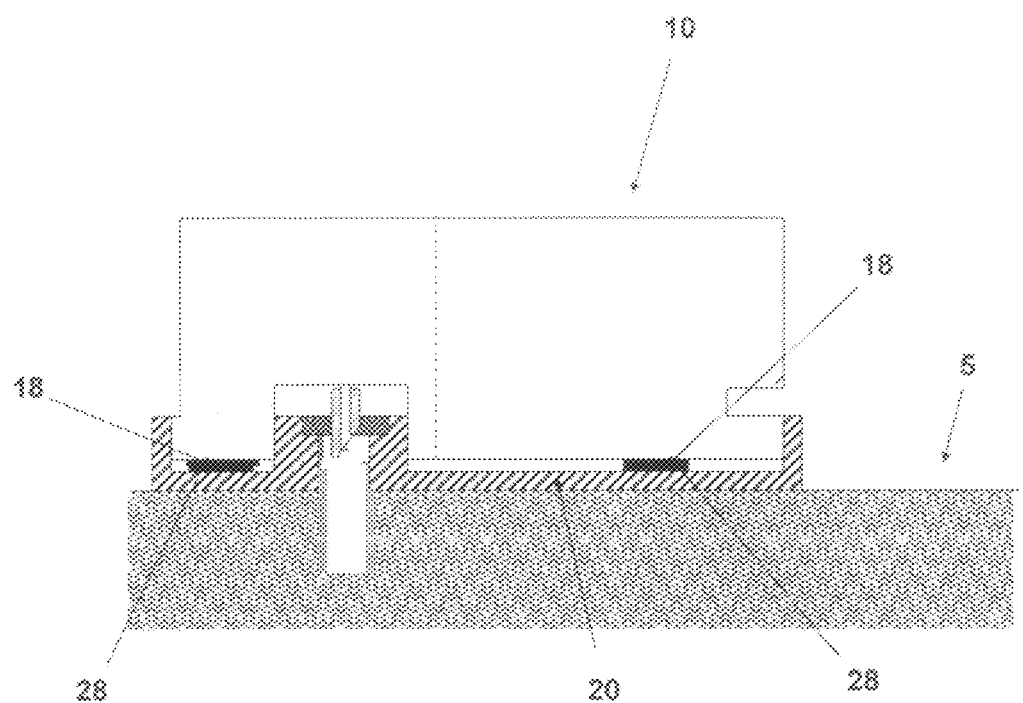
Figure 22C:
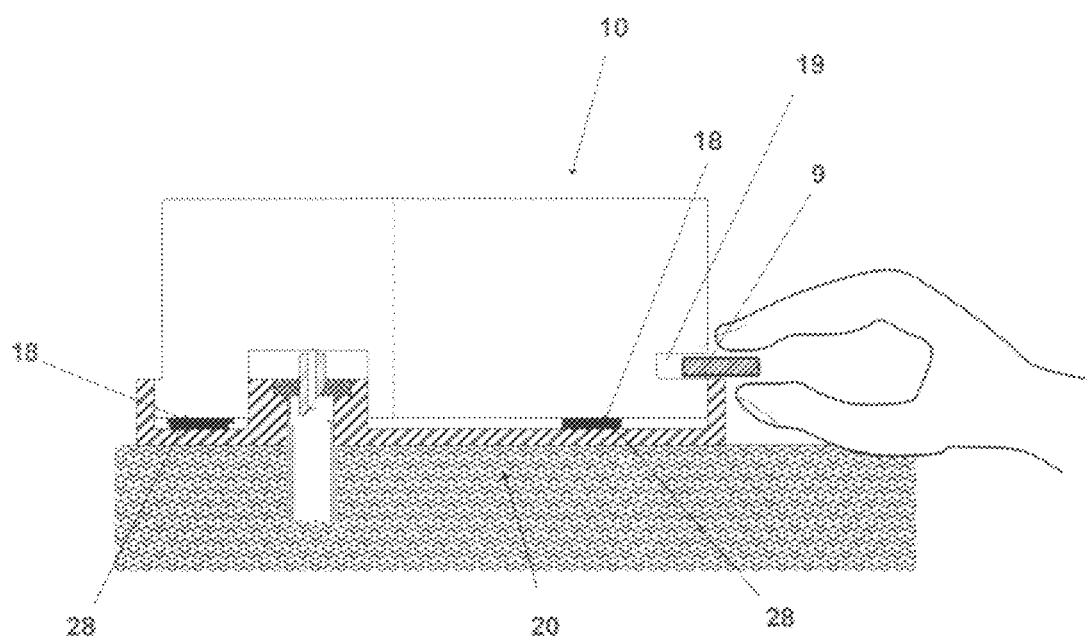

FIGS. 22A-22C show another embodiment of a fluid delivery device and of a method for connecting a patch unit (10) and a needle unit (20). In this embodiment the patch unit (10) and the needle unit (20) are connectable by virtue of magnetic forces. The patch unit (10) comprises a reusable part (100) and a disposable part (200). The needle unit (20) comprises a cradle (300) and a well portion (310). FIG. 22A shows patch unit (10) being brought to the needle unit so as to connect it to the needle unit (20). Magnetic strips (18) are provided at several locations of the bottom surface of the patch unit (10). Magnetic strips (28) are provided at corresponding locations of the upper side of the cradle (300). Cradle (300) is configured with supporting walls (302) protruding upwardly and parallel to the outside surface of the well portion (310). The exit port (210) of the patch unit (10) is configured to match the periphery of the wall portion (310). By virtue of the supporting walls (302) and the well portion (310) the patch unit (10) can be properly positioned on the cradle (300). FIG. 22B shows that connection between the two parts is maintained by magnetic attraction forces of the magnetic strips (18) and (28). FIG. 22C shows disconnection of patch (10) from needle unit (20). This may be affected by placing a thin separating means (9) such as a coin or pin within a dedicated recess (19) provided at the patch unit (10). In principle connection may be achieved by using any other suitable connective material instead of magnetic strips, such as Velcro® Adhesives (e.g., comprising hooks and loops), or the like.

FIGS. 23A-23E show another embodiment of a fluid delivery device and of a method for connecting a patch unit (10) and a needle unit (20). In this embodiment the patch unit (10) is securable on the needle unit (20) by virtue of a trap-like mechanism (an example of which is described below), which, according to some embodiments, is (for example) a structure utilizing one or more catches/recesses/grooves to receive corresponding swing arms (arms)—at least a portion of the swing arm is captured by a corresponding groove thereby "trapping" the patch within the cradle. Accordingly, the patch unit (10) comprises a reusable part (100) and a disposable part (200). The needle unit (20)

comprises a cradle (300) and a well portion (310). Swiveling arms (302) terminated by hooked ends (303) are provided on the needle unit (20) and corresponding grooves (12) are provided on the patch unit (10).

Figure 23A:
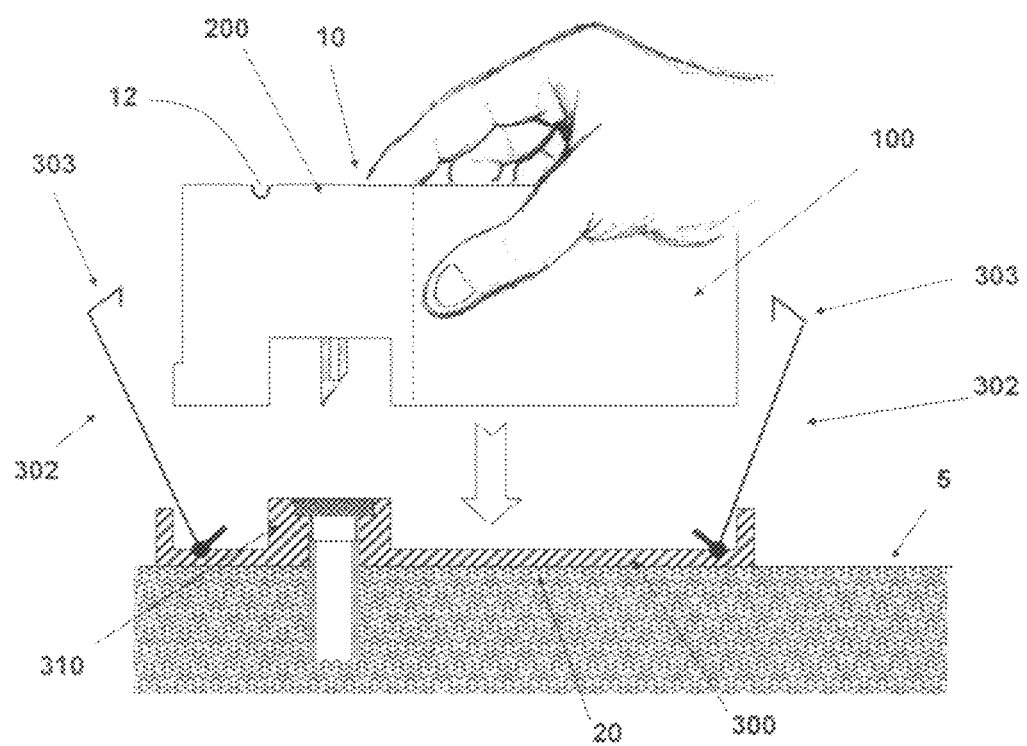
FIG. 23*a-e* are transverse cross-sectional views and perspective views of an alternative embodiment of patch-cradle connection/disconnection by virtue of a trap-like mechanism.
Figure 23B:
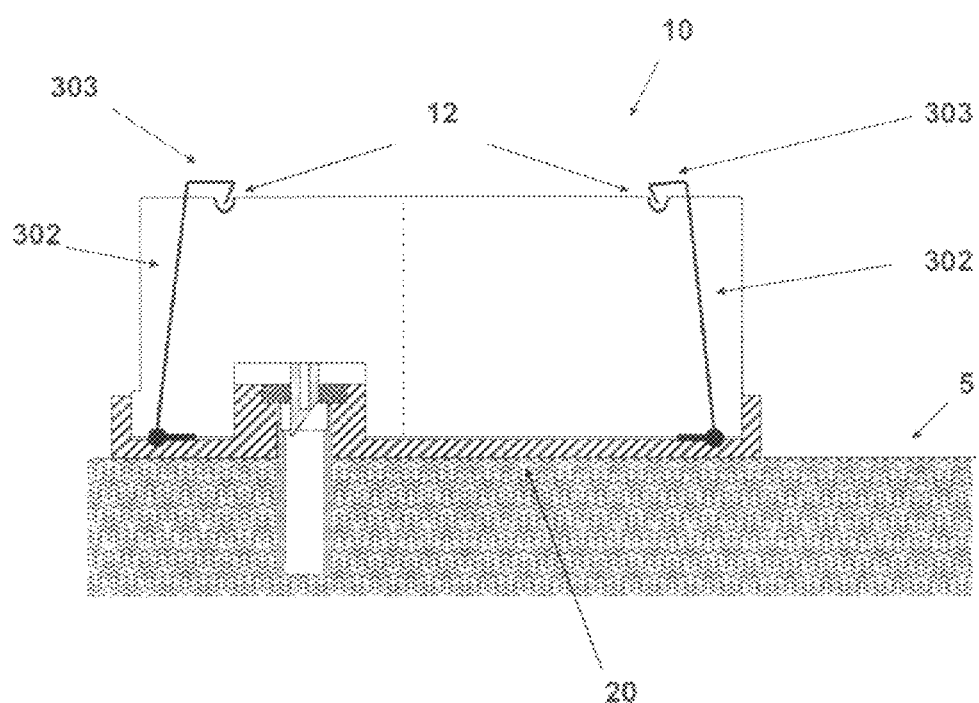

FIG. 23A shows connection of patch unit (10) and needle unit (20) by arms (302). FIG. 23B shows patch unit (10) being secured by arms (302) which have been swiveled so as the hooked ends (303) have entered within the grooves (12, 303) in order to lock the patch unit on the cradle.

Figure 23C:
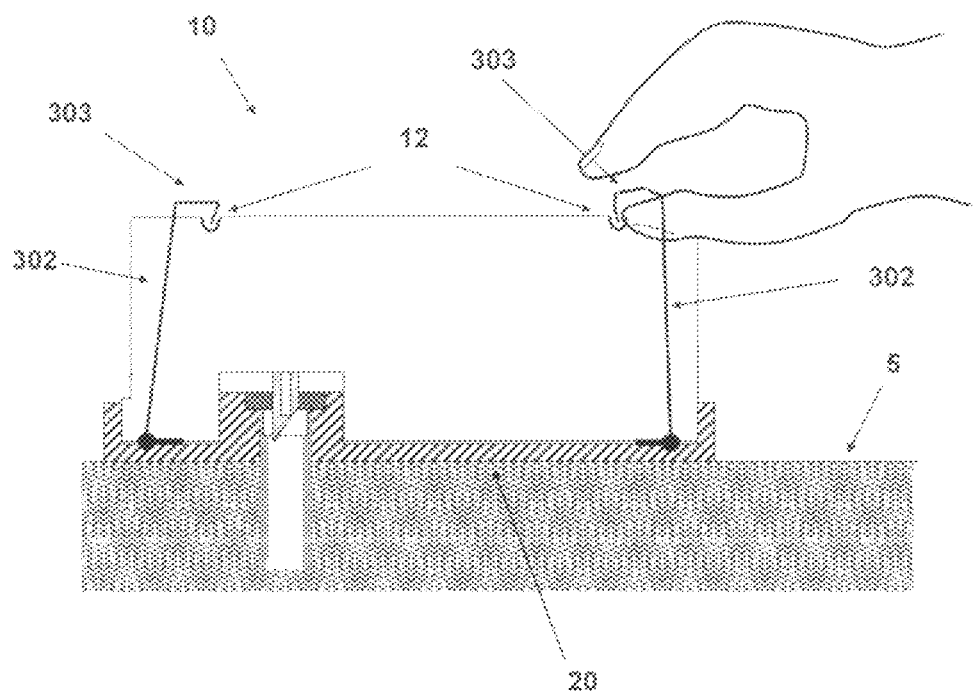
Figure 23D:
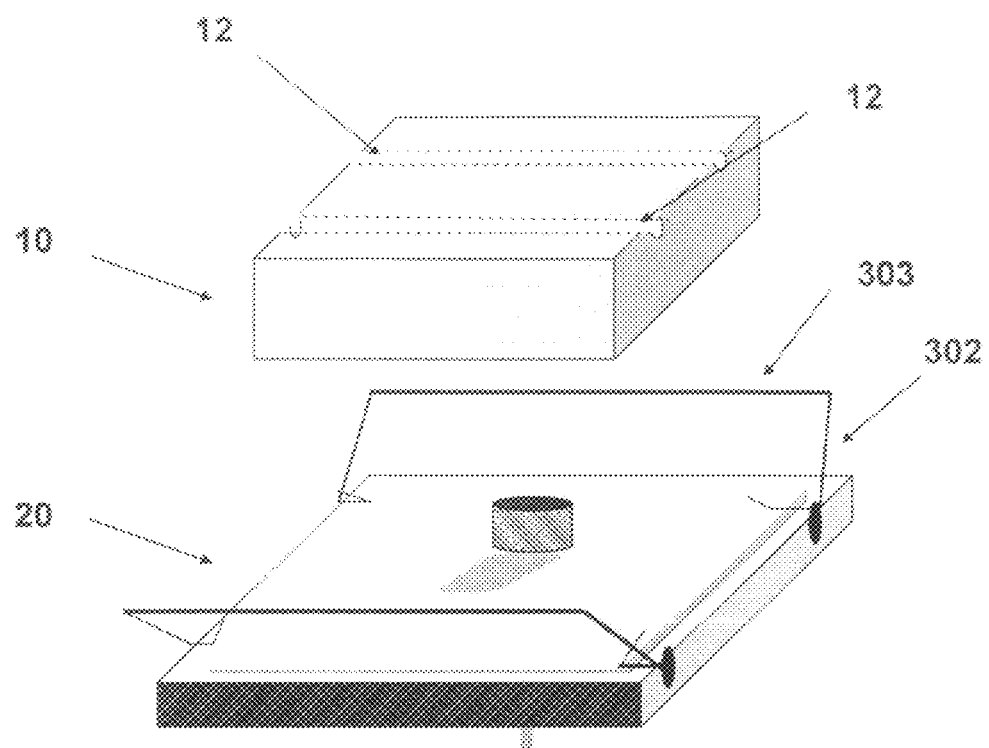
Figure 23E:
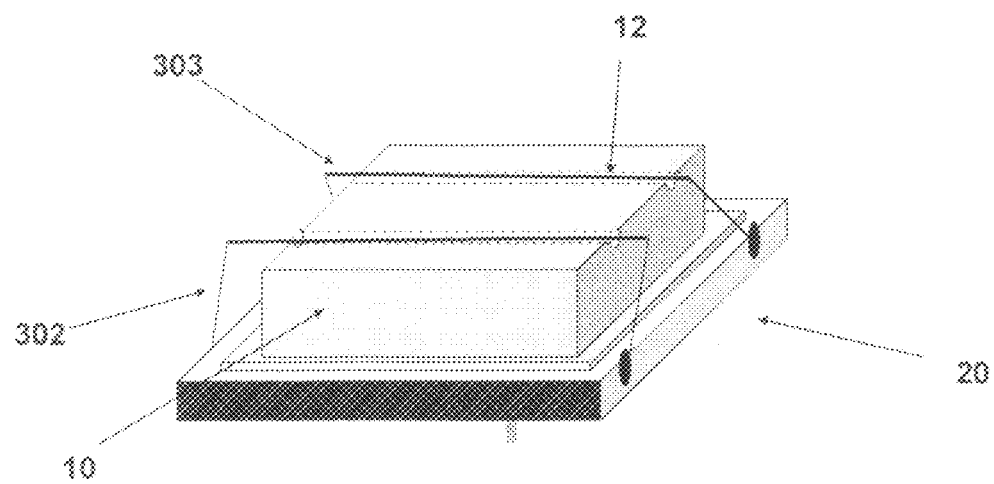

FIG. 23C shows disconnection of patch (10) by swiveling the arms (302) until the hooked ends (303) exit the grooves (12) and release the patch unit (10). FIG. 23D shows perspective view of the patch unit (10) being released and disconnected from the cradle. FIG. 23E shows perspective view of the patch unit (10) secured on the cradle (300).

Thus it is seen that devices, systems and methods for delivering therapeutic fluid into the body are provided. Although particular embodiments have been disclosed herein in detail, this has been done by way of example for purposes of illustration only, and is not intended to be limiting with respect to the scope of the appended claims, which follow. In particular, it is contemplated by the inventors that various substitutions, alterations, and modifications may be made without departing from the spirit and scope of the invention as defined by the claims. Other aspects, advantages, and modifications are considered to be within the scope of the following claims. The claims presented are representative of the inventions disclosed herein. Other, unclaimed inventions are also contemplated. The inventors reserve the right to pursue such inventions in later claims.

All patents, patent applications, articles and other published and/or non-published documents referred to in the present disclosure are herein incorporated by reference in their entireties.

We claim:

1. A therapeutic fluid infusion system for delivering a therapeutic fluid to a body of a patient, the system comprising:
   a skin-adherable unit comprising:
      a cradle configured on a first side for adhesion to the skin of the patient,
      wherein the first side has a periphery,
      a cannula, and
      a self-sealable septum disposed within a proximal portion of a well portion,
      wherein a distal portion of the cannula is configured for subcutaneous placement within the body of the patient and wherein the self-sealable septum separates a proximal portion of the cannula from an external environment; and
   a dispensing unit removably attachable to a second side of the skin-adherable unit that is opposite to the first side, the dispensing unit being sized to fully cover over the well portion and the self-sealable septum and comprising:
      a pump,
      a reservoir for containing a therapeutic fluid, and
      a connecting lumen configured to penetrate the self-sealable septum in order to bring the dispensing unit in fluid communication with the skin-adherable unit, wherein the reservoir, at least a portion of the pump and at least a portion of the connecting lumen are contained within a single housing,
   wherein the dispensing unit is provided with an end for engagement with a corresponding end of the cradle via a protrusion along a rear end of the dispensing unit, the corresponding end of the cradle having a corresponding recess, the engagement enabling pivotal movement of the dispensing unit with respect to the cradle such that the pivotal movement results in connection of the dispensing unit to the cradle when a front end of the dispensing unit is pivoted toward the cradle and a notch along the front end of the dispensing unit snappingly engages a latch in the cradle, and the dispensing unit is detachably securable to the cradle upon the connection, wherein the latch is elastically deformable and is configured to detach from the notch in an outward direction upon application of an outward pulling-force that pulls the latch outward of the periphery of the first side of the cradle; and
   a removable cover for covering the skin-adherable unit;
      wherein the cover substantially seals the skin-adherable unit from the external environment when the skin-adherable unit is adhered to the skin of the patient and while the dispensing unit is not connected to the skin-adherable unit, the cover configured to be substantially vertically placeable onto the skin and around the skin-adherable unit to avoid contamination and abrasion of elements protruding from the skin.

2. The system of claim 1, wherein fluid communication between the reservoir and the connecting lumen is established without the use of tubing external to the single housing.

3. The system of claim 1, further comprising a trap-like mechanism having swing arms for removably attaching the dispensing unit to the skin-adherable unit.

4. The system of claim 1, further comprising hooks and loops for removably attaching the dispensing unit to the skin-adherable unit.

5. The system of claim 1, wherein the cannula and the self-sealable septum are configured to be housed, at least in part, within a well.

6. The system of claim 5, wherein the cradle is integral with at least one of the cannula and the well.

7. The system of claim 5, wherein the cradle and the well are configured for matable attachment.

8. The system of claim 5, wherein the well comprises a protrusion having a pass-through bore, wherein the bore is configured for alignment with an opening in the cradle, and wherein the well is configured for receiving an exit port of the dispensing unit.

9. The system of claim 5, wherein at least one of the well and the cannula is directed at an oblique angle relative to at least one of a cradle surface and a skin of the patient.

10. The system of claim 1, wherein the cradle comprises a substantially planar surface, and wherein the planar surface comprises a polymer having an adhesive disposed thereon.

11. The system of claim 1, wherein the dispensing unit comprises one or more buttons or switches for accepting commands from a user for operating the dispensing unit.

12. The system of claim 1, further comprising a penetrating member configured for placement through the cannula, the penetrating member adapted for piercing a skin of the patient to enable the subcutaneous placement of the distal end of the cannula, wherein the penetrating member is removable from the cannula subsequent to the subcutaneous placement.

13. The system of claim 1, wherein the skin-adherable unit is configured for attachment to a cannula insertion device.

14. The system of claim 1, wherein the dispensing unit comprises:

a disposable part comprising the reservoir and the connecting lumen; and
a reusable part comprising at least a portion of the pump.

15. The system of claim 1, further comprising means for detaching the dispensing unit from the skin-adherable unit.

16. The system of claim 1, wherein the entire reservoir is contained within the single housing along with the at least a portion of the pump and the at least a portion of the connecting lumen.

17. The system of claim 1, wherein the dispensing unit further comprises a fluid delivery tube to communicate therapeutic fluid from the reservoir to the connecting lumen.

18. The system of claim 17, wherein the entire fluid delivery tube is contained within the single housing along with the reservoir, the at least a portion of the pump and the at least a portion of the connecting lumen.

19. A therapeutic fluid infusion system for delivering a therapeutic fluid to a body of a patient, the system comprising:
a skin-adherable unit comprising:
a cradle configured on a first side for adhesion to the skin of a patient,
a cannula, and
a self-sealable septum disposed within a proximal portion of a well portion,
wherein a distal portion of the cannula is configured for subcutaneous placement within the body of the patient and wherein the self-sealable septum separates the proximal portion of the cannula from an external environment; and
a dispensing unit removably attachable to a second side of the skin-adherable unit that is opposite to the first side, the dispensing unit being sized to fully cover over the well portion and the self-sealable septum and comprising:
a single housing or a plurality of integrally connectable housings, a pump,
a reservoir for containing a therapeutic fluid to be dispensed by the dispensing unit into the body of the patient, and
a connecting lumen configured to penetrate the self-sealable septum in order to bring the dispensing unit in fluid communication with the skin-adherable unit,
wherein the pump, the reservoir and at least a portion of the connecting lumen are contained within the single housing or within the plurality of integrally connectable housings
wherein the dispensing unit is provided with an end for engagement with a corresponding end of the cradle via a protrusion along a rear end of the dispensing unit, the corresponding end of the cradle having a corresponding recess, the engagement enabling pivotal movement of the dispensing unit with respect to the cradle such that the pivotal movement results in connection of the dispensing unit to the cradle when a front end of the dispensing unit is pivoted toward the cradle and a notch along the front end of the dispensing unit snappingly engages a latch in the cradle, and the dispensing unit is detachably securable to the cradle upon the connection; and
a removable cover for covering the skin-adherable unit, wherein the cover substantially seals the skin-adherable unit from the external environment while the dispensing unit is not connected to the skin-adherable unit, the cover configured to be substantially vertically placeable onto the skin and around the skin-adherable unit to avoid contamination and abrasion of elements protruding from the skin.

20. The system of claim 19, wherein:
the dispensing unit comprises:
a disposable part comprising the reservoir and the connecting lumen, and
a reusable part comprising at least a portion of the pump; and
the plurality of integrally connectable housings comprises a disposable part housing and a reusable part housing.

21. The system of claim 20, wherein each of the disposable part housing and the reusable part housing comprises at least one connecting area for removable connection to corresponding connecting areas on the skin-adherable unit.

22. The system of claim 21, wherein the at least one connecting area of the disposable part housing and the at least one connecting area of the reusable part housing include a recess or opening for receiving protruding members provided in the corresponding connecting areas of the skin-adherable unit.

* * * * *